(12) United States Patent
Fuller et al.

(10) Patent No.: US 11,376,389 B2
(45) Date of Patent: Jul. 5, 2022

(54) TRACHEAL TUBE APPARATUS AND METHODS

(71) Applicant: Smart Bridge Medical, Inc., Ann Arbor, MI (US)

(72) Inventors: Kay L. Fuller, Ann Arbor, MI (US); Lisa M. Carver, Farmington Hills, MI (US); Matthew T. Hill, Naperville, IL (US); Michael M. Hotta, Novi, MI (US); Laura G. Kruger, Okemos, MI (US); Alexander C. Waselewski, Sterling Heights, MI (US)

(73) Assignee: Smart Bridge Medical, Inc., Ann Arbor, MI (US)

( * ) Notice: Subject to any disclaimer, the term of this patent is extended or adjusted under 35 U.S.C. 154(b) by 650 days.

(21) Appl. No.: 16/436,801

(22) Filed: Jun. 10, 2019

(65) Prior Publication Data
US 2019/0290876 A1 Sep. 26, 2019

Related U.S. Application Data

(63) Continuation-in-part of application No. 15/832,657, filed on Dec. 5, 2017, now Pat. No. 10,328,227.
(Continued)

(51) Int. Cl.
*A61M 16/08* (2006.01)
*A61M 16/04* (2006.01)
*A61M 16/20* (2006.01)

(52) U.S. Cl.
CPC .... *A61M 16/0816* (2013.01); *A61M 16/0459* (2014.02); *A61M 16/0465* (2013.01);
(Continued)

(58) Field of Classification Search
CPC .......... A61M 16/0816; A61M 16/0486; A61M 16/0465; A61M 16/0459; A61M 16/209;
(Continued)

(56) References Cited

U.S. PATENT DOCUMENTS 2,860,633 A  11/1958 Phillips
3,169,529 A   2/1965 Koenig
(Continued)

FOREIGN PATENT DOCUMENTS

GB          649230 A1 * 11/1949
WO    WO2008/015094 A1    2/2008

OTHER PUBLICATIONS

Dale Medical Products, Inc.; Dale® Tracheostomy Tube Holders (product information); 2 pgs. © 2014; retrieved Jun. 7, 2016 from the internet: hftp://dalemed.com/Products/TracheostomyTubeHolder.aspx.
(Continued)

*Primary Examiner* — Victoria Murphy
(74) *Attorney, Agent, or Firm* — Shay Glenn LLP

(57) ABSTRACT

A tracheal tube (e.g., an endotracheal tube) includes an inserting cannula (that may be able to swivel), and wherein the inserting cannula is connected to an elbow adaptor through a Bayonet Neill-Concelman (BNC) connection. The BNC connection may provide more secure connection of the corresponding components and may be able to withstand greater amounts of force exerted on them without becoming detached from each other. The elbow adapter may further be coupled to a pressure release valve that will alleviate pressure buildup within the tracheal tube.

15 Claims, 20 Drawing Sheets

Related U.S. Application Data which is a continuation of application No. 15/146,751, filed on May 4, 2016, now Pat. No. 9,833,588.

(60) Provisional application No. 62/156,819, filed on May 4, 2015, provisional application No. 62/780,855, filed on Dec. 17, 2018.

(52) U.S. Cl.
CPC .... *A61M 16/0488* (2013.01); *A61M 16/0497* (2013.01); *A61M 16/209* (2014.02)

(58) Field of Classification Search
CPC ........ A61M 16/0497; A61M 2205/584; A61M 16/20; A61M 16/0488; F16K 15/148
USPC ...................... 285/148.15; 137/854; 403/349
See application file for complete search history.

(56) References Cited

U.S. PATENT DOCUMENTS

| | | | | |
|---|---|---|---|---|
| 3,869,218 | A | * | 3/1975 | Stoeber ................ F16B 7/0413 285/402 |
| 4,304,228 | A | | 12/1981 | Depel |
| 4,305,180 | A | * | 12/1981 | Schwartz ................ F16B 21/04 403/349 |
| 4,306,743 | A | * | 12/1981 | Hinshaw ............... F16L 37/248 285/260 |
| 4,424,806 | A | | 1/1984 | Newman et al. |
| 4,449,523 | A | | 5/1984 | Szachowicz et al. |
| 5,392,775 | A | | 2/1995 | Adkins et al. |
| 6,588,428 | B2 | | 7/2003 | Shikani et al. |
| 8,707,950 | B1 | | 4/2014 | Rubin |
| 9,833,588 | B2 | | 12/2017 | Fuller et al. |
| 10,328,227 | B2 | | 6/2019 | Fuller et al. |
| 2002/0029782 | A1 | * | 3/2002 | Linderoth ......... A61M 16/0465 128/207.15 |
| 2004/0261797 | A1 | | 12/2004 | White et al. |
| 2011/0301685 | A1 | | 12/2011 | Kao |
| 2012/0103342 | A1 | | 5/2012 | Shikani et al. |
| 2012/0199120 | A1 | | 8/2012 | Matlock |
| 2013/0133644 | A1 | | 5/2013 | Rosekrans et al. |
| 2014/0150798 | A1 | | 6/2014 | Fong et al. |
| 2014/0276178 | A1 | | 9/2014 | Simon |
| 2014/0283827 | A1 | | 9/2014 | Flower |

OTHER PUBLICATIONS

ECRI Institute; Top 10 Health Technology Hazards for 2015; Health Devices; 33 pgs.; Nov. 2014.

Intersurgical; Double Swivel Elbow (product page); 1 pg.; retrieved from the internet: http://www.intersurgical.com/products/airway-management/double-swivel-elbows; print/retrieval date Jun. 9, 2016.

Medtronic; ShileyTM Tracheostomy Tubes with Disposable Inner Cannula (prcduct page); 1 pg.; retrieved from the internet: http://www.medtronic.com/covidien/products/tracheostomy/shirley-tracheostomy-tubes-with-disposable-inner-cannula; print/retrieval date Jun. 9, 2016.

Medtronic; StrongholdTM Anti-Disconnect Devices (product page); 1 pg.; retrieved from the internet:http://www.medtronic.com/covidien/products/tracheostomy/stronghold-anti-disconnect-devices; print/retrieval date Jun. 9, 2016.

\* cited by examiner

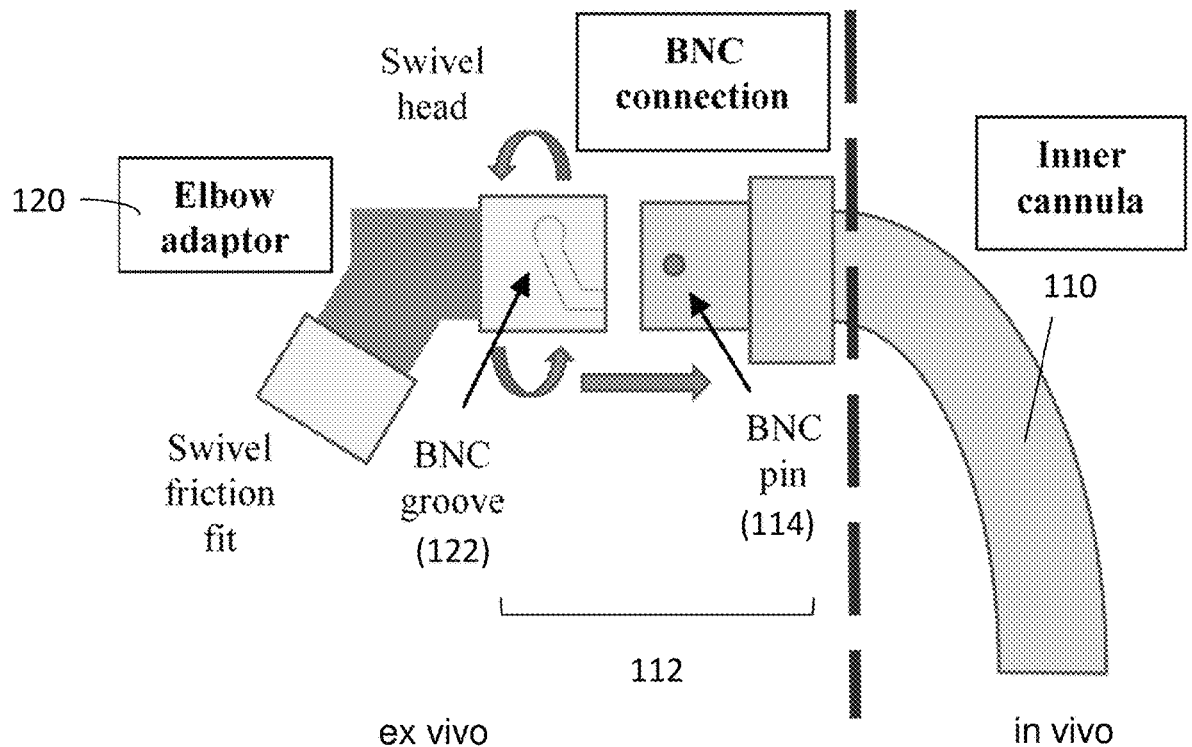
FIG. 11
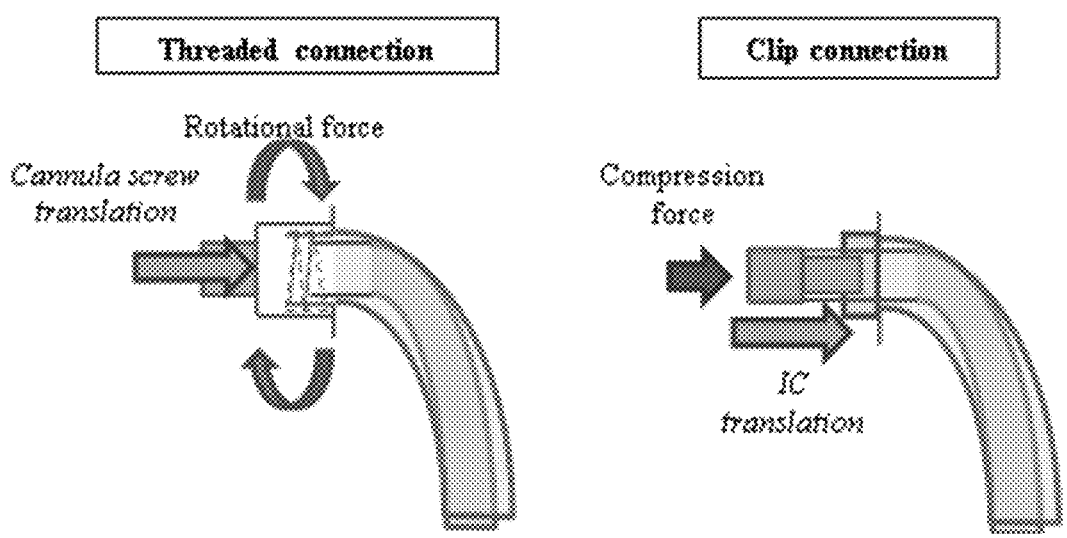
FIG. 13A                    FIG. 13B

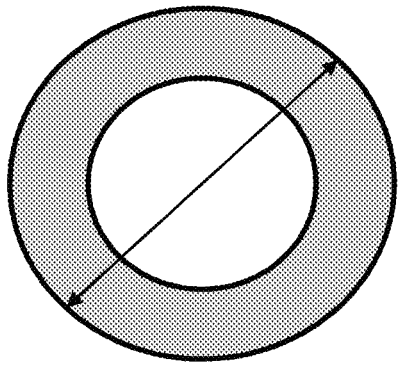
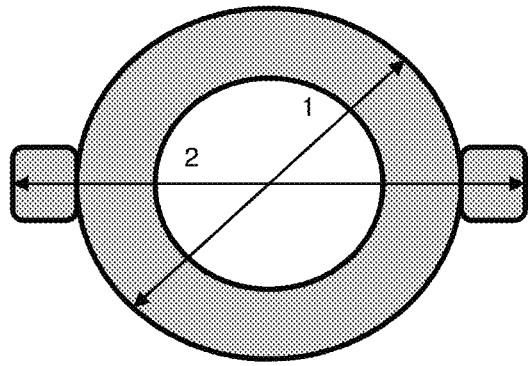
FIG. 18A
FIG. 18B
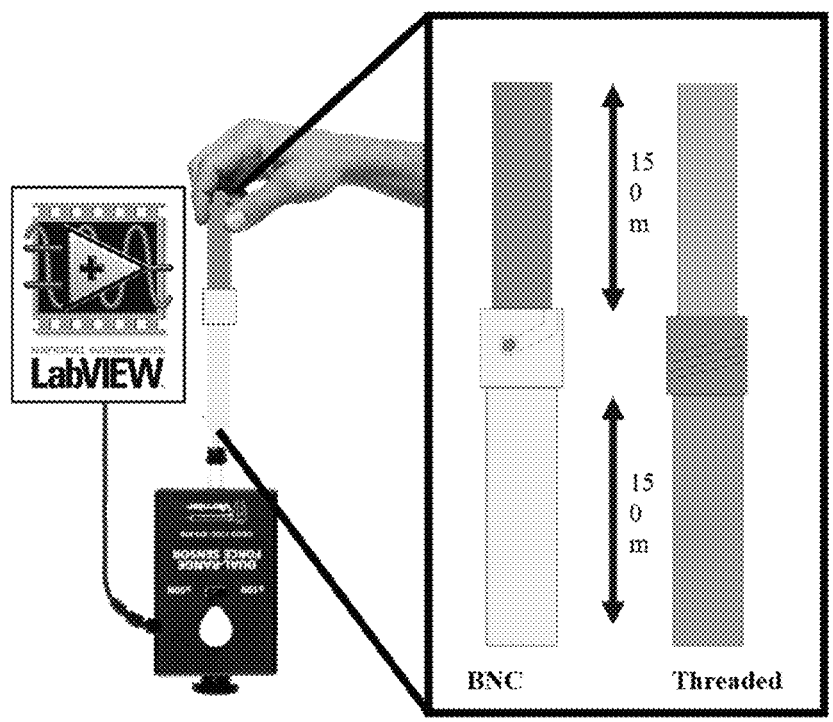
FIG. 19

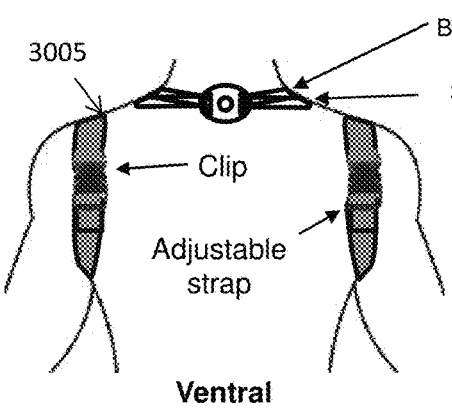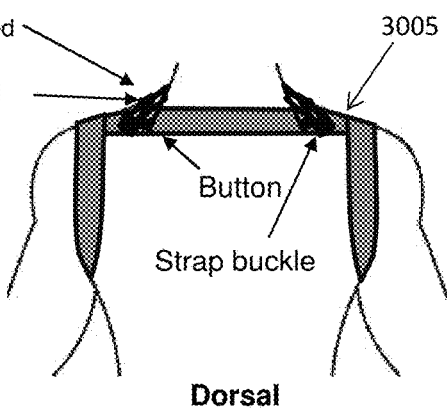
FIG. 30A  FIG. 30B
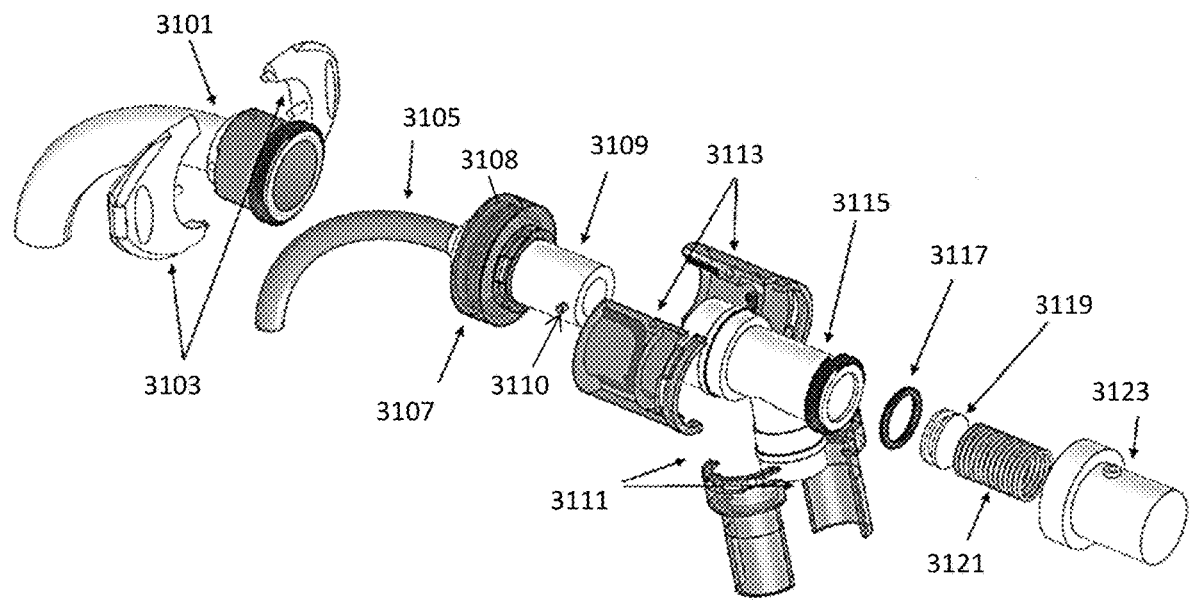
FIG. 31

TRACHEAL TUBE APPARATUS AND METHODS

CROSS REFERENCE TO RELATED APPLICATIONS

This patent application is a continuation-in-part to U.S. patent application Ser. No. 15/832,657, filed on Dec. 5, 2017, titled "TRACHEAL TUBE APPARATUS AND METHODS," now U.S. Patent Application Publication No. 2018/0093061, which is a continuation of U.S. patent application Ser. No. 15/146,751, filed May 4, 2016, titled "TRACHEAL TUBE APPARATUS AND METHODS," now U.S. Pat. No. 9,833,588, which claims priority to U.S. Provisional Patent Application No. 62/156,819, filed on May 4, 2015 and titled "TRACHIAL TUBE APPARATUS AND METHODS."

This patent application also claims priority to U.S. Provisional Patent Application No. 62/780,855, filed on Dec. 17, 2018, titled "TRACHEAL TUBE APPARATUS AND METHODS." Each of these application and patents is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are tracheal tubes, as well as methods of using and constructing them.

BACKGROUND

Tracheal tubes are typically a catheter that is inserted into the patient's trachea for the primary purpose of establishing and maintaining a patent airway and to ensure the adequate exchange of oxygen and carbon dioxide via a breathing (anesthesia/ventilator) circuit. In general, tracheal tubes include endotracheal tubes (ET or ETT), which may be inserted through the mouth (orotracheal) or nose (nasotracheal), and tracheostomy tubes, that may be inserted into a tracheostomy stoma (e.g., following a tracheotomy). Tracheal tubes maintain a patent lumen within the patient's trachea. Tracheal tubes (endotracheal and tracheostomy) are commonly used for airway management in the settings of general anesthesia, critical care, mechanical ventilation, and emergency medicine.

A tracheotomy is a medical procedure for patients requiring mechanical ventilation in which an opening is created through the neck into the trachea creating a stoma or tracheostomy. A tracheostomy tube, comprised of an inner cannula within an outer cannula, is placed into the stoma and connected by an elbow adaptor through a breathing circuit to the ventilator. Nearly 100,000 tracheostomies are performed in the US annually. Many patients with tracheostomies are ventilator dependent, tetraplegic patients with compromised lung capacity and are unable to fix any ventilator disconnections or other airflow disruptions on their own leaving them with as little as two minutes to live without ventilation.

The majority of commercially available devices typically employ friction fit connections in the ventilator circuit, a clip connection between the cannulas, and/or a Velcro securement (e.g., between the tracheostomy tube and the patient's neck, the ET and the patient's mouth/nose, etc.). These connections are designed for quick attachment, but are prone to frequent unintended disconnections. A tracheostomy tube and ventilator circuit less prone to unintended ventilator disconnections can provide the necessary safety measures to prevent these catastrophic events.

There is a need for systems that minimize unintended airflow disruptions of the ventilator circuit, thereby increasing safety, comfort, and peace-of-mind for the patient.

SUMMARY

Described herein are tracheal tubes that may address the needs discussed above. These tracheal tubes may be configured as either endotracheal tubes or tracheostomy tubes.

The resulting prototype, described herein, may include one or more of: a Bayonet Neill-Concelman ("BNC") type connection for the inner cannula to elbow adaptor connection, a threaded connection for the inner cannula to outer cannula connection, and a pressure release valve as a part of the elbow adaptor. This combination of elements may be important as they have surprisingly beneficial effects in combination. For example, the BNC connection improves strength of the connection and confirms correct assembly, particularly in combination with the threaded connection to improve usability and reduces force into the stoma. The pressure release valve helps mitigate high airway pressures that may cause disconnections or lung damage.

Verification and validation testing demonstrated that the initial prototypes described herein fulfilled all requirements tested except compatibility with current art, weight of the current design, and air pressure tolerance. Of particularly significance was the surprisingly enhanced ease of use and reliability. The prototypes described herein took the same amount of time to assemble and disassemble by both care providers and untrained lay people; users made more assembly errors with currently available commercial devices compared to the devices described herein.

In general, described herein are designs for a tracheal tube that improves upon existing tracheal tube design. Unlike other tracheal tube assemblies that may become detached by normal movement or may be incompletely attached by the operator, the tracheal tube design described below ensure that the components of the tracheal tube are properly attached so that the patient is provided with enough air for adequate respiration.

In general, these tracheal tubes may include an outer cannula, an inner cannula, and an elbow adapter. The outer cannula has an outer cannula proximal end and an outer cannula distal end. The outer cannula distal end having outer cannula threads. The inner cannula has an inner cannula proximal end and an inner cannula distal end and is configured to be inserted into the outer cannula. The inner cannula further includes an inner cannula coupler for mating with the outer cannula threads. The inner cannula includes at least one ridge on the inner cannula distal end and a swivel piece configured to rotate around the at least one ridge. The swivel piece is external to the inner cannula and configured to rotate without moving the inner cannula within the outer cannula. Typically, the connection between the inner and the outer cannula has a connection strength greater or equal to 45 N.

The tracheal tube may be configured as an endotracheal tube; in some variations the tracheal tube is configured as a tracheostomy tube.

The elbow adapter is configured to couple the inner cannula with a mechanical ventilator for providing air to a patient. The elbow adapter is secured to the inner cannula through a Bayonet Neill-Concelman (BNC) type connection. The BNC connection includes two pins on the inner cannula distal end and two corresponding channels on the elbow adapter. In some variations, the two corresponding channels are arcs that curve approximately ninety degrees. The elbow adapter further includes a coupling or mating mechanism for connecting the tracheal tube to a mechanical ventilator. The elbow adapter and ventilator connection is also configured to swivel.

The tracheal tube may further include a pressure release valve for releasing excess pressure. The pressure release valve includes a casing with an aperture, a spring, and pressure release spring disc. The pressure release valve also includes a seal that mates with the pressure release valve spring disc. The pressure release valve is coupled to the elbow adapter through a pressure release valve and elbow adapter threaded connection. The seal is configured to push back at high pressures and compress the spring. This exposes the aperture and allows air to escape through the aperture. Similar to the inner and the outer cannula connection, the elbow adapter and the inner cannula connection has a connection strength of greater or equal to 45 N.

In general, the tracheal tubes described herein include an outer cannula having an outer cannula proximal end and an outer cannula distal end. The outer cannula distal end having outer cannula threads. An inner cannula is configured to insert into the outer cannula and has an inner cannula proximal end and an inner cannula distal end. The inner cannula distal end has inner cannula threads for mating with the outer cannula threads. The connection between the inner and the outer cannula having a connection strength of greater or equal to 45 N.

An elbow adapter is configured to couple the inner cannula with a mechanical ventilator for providing air to a patient. A Bayonet Neill-Concelman (BNC) connector configured to secure the elbow adapter to the inner cannula. A pressure release valve configured to release excess pressure. The inner cannula further includes at least one ridge on the inner cannula distal end, a swivel piece configured to rotate around the at least one ridge. The swivel piece is external to the inner cannula and configured to rotate without moving the inner cannula within the outer cannula. The BNC connection comprises two pins on the inner cannula distal end and two corresponding channels on the elbow adapter. The two corresponding channels are arcs that curved 90 degrees. The inner cannula and the elbow adapter having a connection strength of greater or equal to 45 N.

The pressure release valve comprises a casing with an aperture, a spring, and a pressure release valve spring disc. The pressure valve further includes a seal mated with the pressure release valve spring disc, wherein the seal is configured to push back at high air pressures, compress the spring, and allow air to escape through the aperture. The pressure release valve is coupled to the elbow adapter through a pressure release valve-elbow adapter threaded connection. The tracheal tube further includes a ventilator-elbow adaptor connection that is adapted to swivel. The pressure release valve is configured to release pressure above 65 cm $H_2O$.

Also disclosed herein are methods of using a tracheal tube within a patient. The methods generally include inserting an inserting cannula into a patient's tracheal opening (nose and/or mouth), where the inserting cannula has a proximal end and a distal end, the distal end having threads. In some variations an adapter may then be connected as described above (and optionally locked to the inserting cannula); alternatively, the adapter may be already locked onto the inserting cannula). This may be followed by inserting an inserting cannula into the outer cannula, where the inner cannula having an inner cannula proximal end and an inner cannula distal end, the inner cannula distal end having inner cannula threads for mating with the outer cannula threads. Then, coupling an elbow adapter to the inner cannula through a Bayonet Neill-Concelman (BNC) connection, where the elbow adapter is coupled to a pressure release valve and where the elbow adapter is coupled to a mechanical ventilator through an elbow adapter-ventilator connection. The ventilator-elbow adaptor connection that is adapted to swivel. And finally, monitoring pressure within the tracheal tube such that when a predetermined pressure level is exceeded, the pressure release valve will open and release pressure within the tracheal tube until the pressure is at or below the predetermined pressure level.

As mentioned earlier, the inner cannula further includes at least one ridge on the inner cannula distal end, a swivel piece configured to rotate around the at least one ridge, where the swivel piece is external to the inner cannula and configured to rotate without moving the inner cannula within the outer cannula. The BNC connection comprises two pins on the inner cannula distal end and two corresponding channels on the elbow adapter. The two corresponding channels are arcs that curved 90 degrees. The pressure release valve includes a casing with an aperture, a spring, and a pressure release valve spring disc. The pressure release valve comprising a seal mated with the pressure release valve spring disc, where the seal is configured to push back at high air pressures, compress the spring, and allow air to escape through the aperture. The pressure release valve is also coupled to the elbow adapter through a pressure release valve-elbow adapter threaded connection. The connection between the inner and the outer cannula having a connection strength of greater or equal to 45 N. The connection between the inner cannula and the elbow adapter having a connection strength of greater or equal to 45 N. The pressure release valve is configured to release pressure above 65 cm $H_2O$.

In any of the apparatuses described herein the inserting cannula (which may be referred to in some of the examples provided as the outer cannula) may be coupled directly to the elbow adapter or indirectly thorough an adapter (which may be referred to herein in some variations as an inner catheter). For example, a tracheal tube assembly may include: an inserting cannula having a proximal end and a distal end, the distal end having two or more pins extending laterally from a sidewall of the distal end; and an elbow adapter configured to couple the inserting cannula with a mechanical ventilator for providing air to a patient; a pressure release valve on the elbow adapter configured to mitigate high airway pressures that may cause disconnections or lung damage; and a Bayonet Neill-Concelman (BNC) connector configured to secure the elbow adapter to the inserting cannula, wherein a locking region of the BNC is transparent or translucent and is configured to change color when the BNC is engaged with the inserting cannula. A tracheal tube assembly may include: an inserting cannula having a proximal end and a distal end, the distal end having two or more pins extending laterally from a sidewall of the distal end; an elbow adapter configured to couple the inserting cannula with a mechanical ventilator for providing air to a patient; a Bayonet Neill-Concelman (BNC) connector on the elbow adapter configured to secure the elbow adapter to the inserting cannula wherein a locking region of the BNC is transparent or translucent and is configured to change color when the BNC is engaged with the inserting cannula; and a pressure release valve on the elbow adapter configured to release excess pressure to mitigate high airway pressures that may cause disconnections or lung damage.

In any of these apparatuses, the connection between the inserting cannula and the elbow adapter may have a connection strength of greater or equal to 45 N. The connection strength maybe measured in Newton's. Alternatively, the connection strength may be measured as a pressure (e.g., in $N/m^2$ or kPa). The pressure release valve may be configured to release pressure above 65 cm $H_2O$.

Also described herein are methods of using a tracheal tube within a patient that include: inserting a cannula into a patient's mouth or nose, wherein the cannula has a proximal end and a distal end, the distal end having two or more pins extending laterally from a sidewall of the distal end; coupling an elbow adapter to the cannula through a Bayonet Neill-Concelman (BNC) connection, wherein the elbow adapter is coupled to a mechanical ventilator through an elbow adapter-ventilator connection; and operating the tracheal tube so that a force greater than or equal to 45 N must be applied to separate the cannula from the elbow adapter.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 11 illustrates the BNC connection layout of a tracheal tube device as described herein (allowing connection between the combined, as shown in FIG. 10, inner and outer cannulas and the elbow adapter region.

FIGS. 13A and 13B shows a comparison in the force diagrams between threaded (left) and clip (right) connections.

FIGS. 18A and 18B illustrates a comparison of dimensional compatibility test result between a friction-fit connection tracheal tube and a next-gen device having a BNC connection.

FIG. 19 illustrates one example of an experimental set-up for testing the apparatuses described herein (showing testing for force at soma).

FIGS. 30A and 30B illustrate a shoulder harness as described herein.

FIG. 31 is an exploded view of one variation of a next-gen tracheal tube apparatus as described herein.

DETAILED DESCRIPTION

Described herein are tracheal tubes with improved pull-out resistance. These tubes may be configured for insertion into a patient's mouth or nose (e.g., endotracheal tubes) and/or for insertion into a tracheal opening (e.g., a tracheostomy tube), such as that formed by a tracheostomy. A tracheostomy is a medical procedure used for patients with a prolonged or emergent need for mechanical ventilation in which an opening is created through the neck into the trachea creating a stoma or tracheostomy. FIGS. 1 to 8 illustrate prior art tracheal tubes, including those configured as tracheostomy tubes. A tracheostomy tube such as the one shown in FIG. 1 may be placed into the stoma and connected to a ventilator by a breathing circuit. More than 83,000 tracheostomies were placed in 1999 with a primary need for mechanical ventilation in chronically ill patients. Conditions that may require mechanical ventilation with a tracheostomy include neurological conditions (e.g., tetraplegia), chronic obstructive pulmonary disease, myasthenia gravis, Guillain-Barre syndrome, asthma, emphysema, and sarcoidosis.

The trach tube, breathing circuit, and ventilator are typically connected via friction fits. Breathing cycles created by the ventilator pushes air into the patient's trachea and opens the lungs. When there is no pressure being produced, exhaled carbon dioxide is allowed to leak out through the circuit from a unidirectional valve. The trach tube is secured to the patient through a tracheostomy tube holder or collar. The collar loops through two holes on either side and held in place by Velcro (e.g., FIG. 2).

Figure 4:
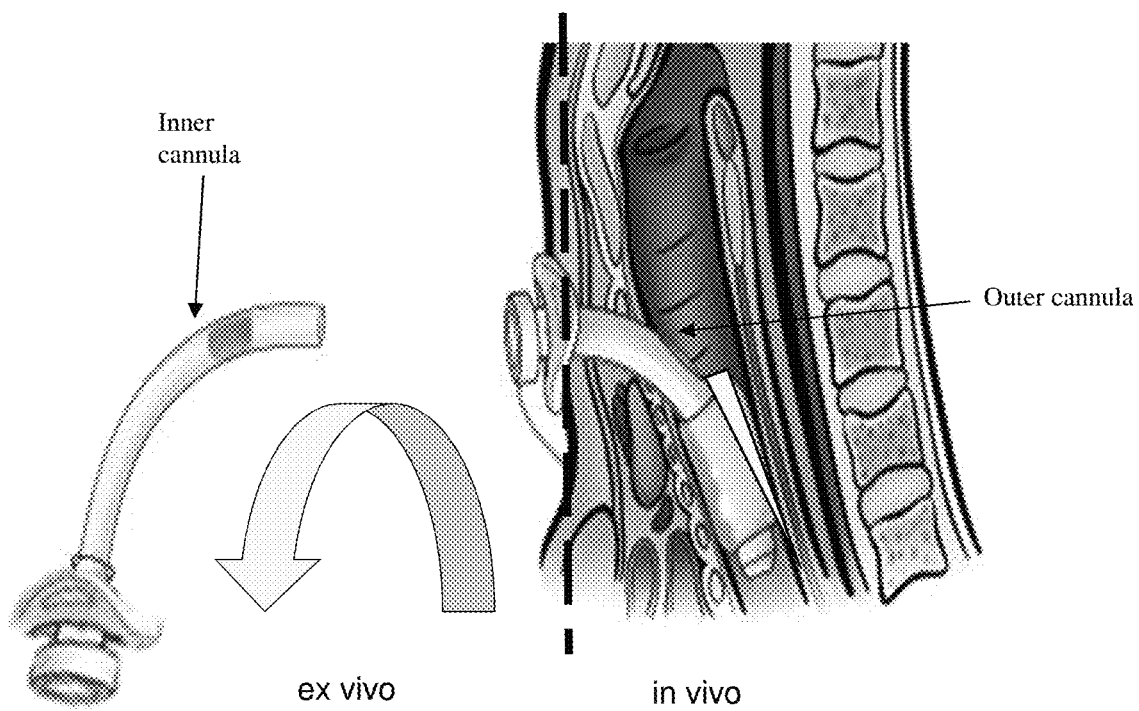
FIG. 4 illustrates dislodgement of a prior art tracheotomy tube.

The limitations with the current technology are discomfort, unintended disconnections (e.g., see FIG. 3), and dislodgements (see, e.g., FIG. 4). Described herein are next-generation ("next-gen" or prototype) tracheal tubes devices, configured as either or both endotracheal tubes or tracheostomy tubes, that address the problems with prior art devices described above. Some variations of these devices were designed in reference to a tetraplegic patient that has sensation only above the neck; in such patients existing collar devices can cause a strangling sensation and pressure sores because of the tightness required to secure the trach tube.

Intended disconnections of the ventilator circuit are necessary for suctioning, but unintended disconnections occur more often than they should due to lubrication of the friction fit between the elbow adaptor (EA) and inner cannula (IC) from tracheal secretions. Disconnections typically need to occur when there is a large, sudden force on the circuit such as something catching on the circuit; otherwise dislodgement of the tracheal tube can occur. Dislodgement refers to the entire trach tube coming out of the stoma, and it is very dangerous to the patient as improper re-insertion can cause damage to the stoma. Additionally, the whole circuit is heavy and unintended disconnections may occur due to the weight of the device itself.

For both disconnections and dislodgement, the patient is deprived of oxygen, and some vent-dependent patients need to be reconnected within 2 minutes to prevent brain damage or death, leaving patients in an extremely vulnerable state. A 2010 review report in the UK found that 75% of tracheostomy related incidents in hospitals caused identifiable harm and 18% caused greater than temporary harm. Meanwhile, The ECRI Institute reported uncaught ventilator disconnections due to miss-set or missed alarms as the number five hazard within the Top 10 Health Technology Hazards for 2015 report. Finally, possible lung damage can occur due to high pressure from the ventilator. The ventilator turns off if the pressure is high for a prolonged time.

Figure 5:
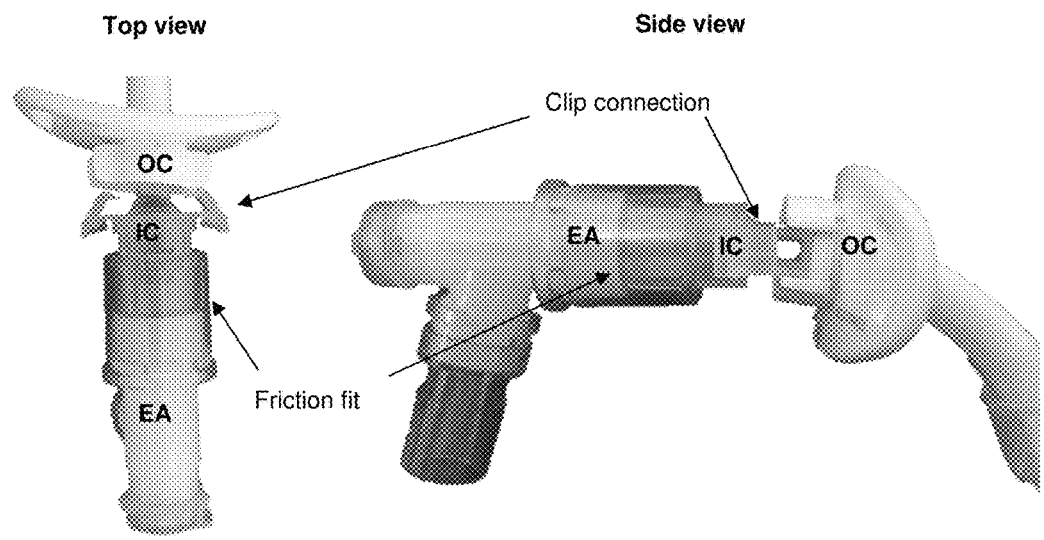
FIG. 5 shows top and side views, respectively of an example of a tracheal tube, including an elbow adaptor (EA) and inner cannula (IC), and outer cannula (OC).
Figure 6:
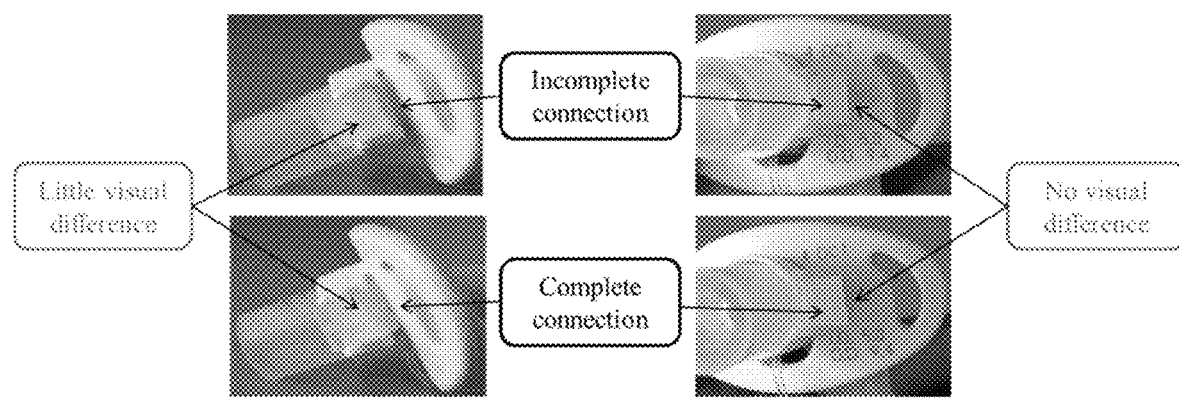
FIG. 6 illustrates a clipping connection showing little visual differences in complete and incomplete connections.
Figure 7:
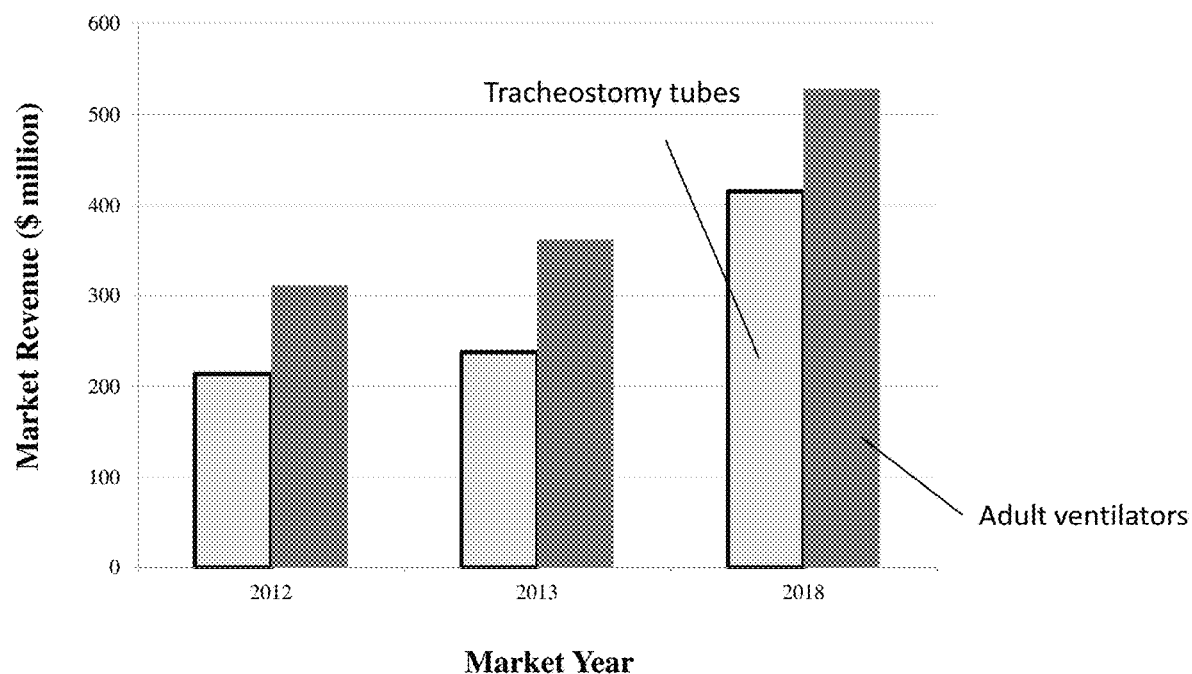
FIG. 7 illustrates market projection for tracheal tubes, indicating an increasing need for improved tracheal tubes such as those illustrated herein.

Prior art devices typically use a clipping connection between the IC and the outer cannula (OC) and friction fit between the IC and EA, as shown in FIG. 5. Both are inadequate for minimizing unintended disconnections and maintaining patient comfort. These clips are visually misleading and require an uncomfortably large force on the patient's throat for complete connection. The clips may falsely appear to be connected together (see, e.g., FIG. 6) when the clip ridge sits on the edge of the OC, which may lead to de-cannulation.

The most common point of disconnection is the friction fit between the IC and the EA. This friction fit has a reduced strength due to lubrication from tracheal secretions and users not twisting the fit together per packaging instructions. Therefore, having emergency disconnections due to excessive force occur at locations other than the EA would be advantageous because more distal locations in the ventilator circuit are less exposed to secretions and will be able to withstand higher forces before disconnecting. Within the UK, a review found that current tracheostomy equipment was implicated in 39% of tracheostomy-related incidents, indicating that the current device design is inadequate for the user. The devices described herein may address the aforementioned issues including unintended disconnections, dislodgment from the trachea, and patient comfort.

Primary beneficiaries for the apparatuses (devices and systems) described herein include ventilator-dependent patients with a tracheostomy, as well as their care providers, respiratory therapists, hospitals, and medical supply companies. The device will primarily be used in the hospital and home. The incidence of tracheostomies is 51.8 per 100,000 US adults per year. Approximately 100,000 tracheostomies are performed in the US annually. Tracheostomy tubes were a $213 million global market in 2013 and are growing at a rate of 11.8% per year with a projected $415 million market by 2018 (see, e.g., FIG. 7). The global market for ventilators was $648 million in 2013 growing at a rate of 7.9% a year with a projected $1.1 billion market by 2018.

Figure 2:
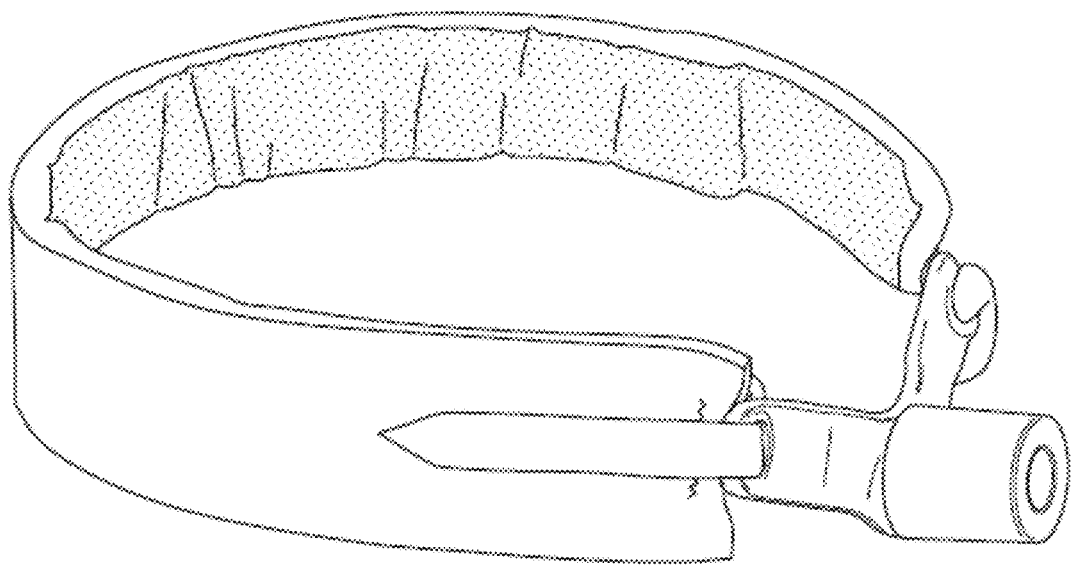
FIG. 2 illustrates one example of a tracheotomy ("trach") tube holder.
Figure 3:
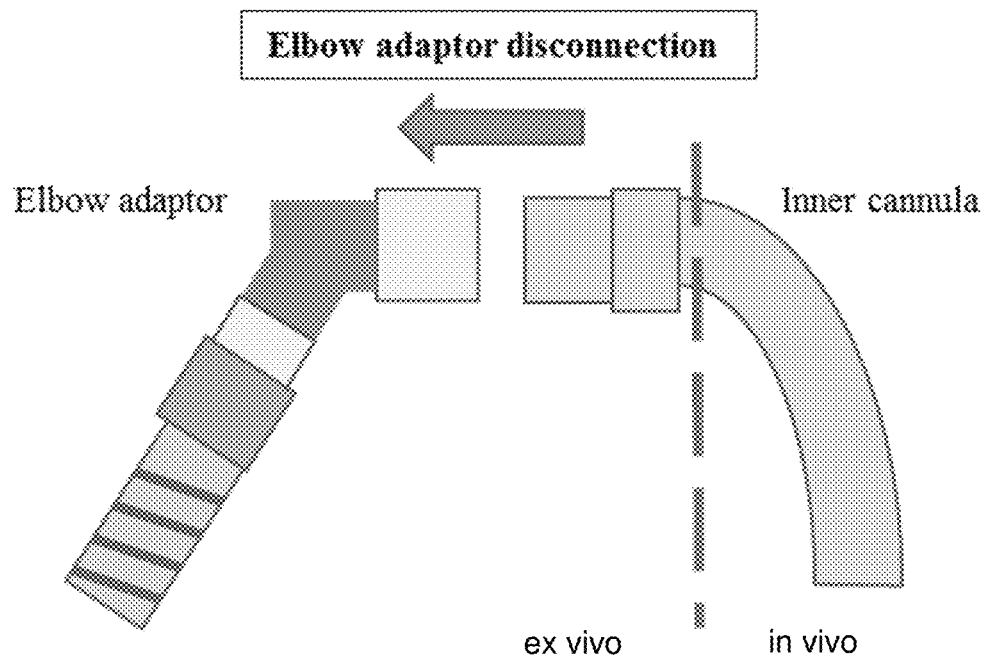
FIG. 3 illustrates disconnection of a prior art tracheotomy tube.

The Dale Tracheostomy Tube holder is the current gold standard on the market with a cost of approximately $3.50-$5.00 per holder. This product includes foam padding with a moisture resistant lining, an elastic panel for expansion, and Velcro loops to hold the tracheostomy tube in place (such as is shown in FIG. 2). Many tracheostomy tube holders on the market have similar designs involving foam padding and Velcro securements and are a variation on the Dale Tracheostomy Tube Holder. Twill ties are a shoelacelike string that is threaded through the faceplate and tied around the neck and are included in tracheostomy tube kits. The Dale Tracheostomy Tube Holder was an improvement over traditional twill ties, however, it collects moisture in the foam padding, contributing to pressure sores and skin infections and, thus, can be uncomfortable for patients.

The Intersurgical Double Swivel EA shown in FIG. 5 is the gold standard prior art device for connecting the IC to the rest of the ventilator circuit with a cost of about $1.96 per adaptor. The proximal end features a friction fit between the IC and EA. The distal end also includes a friction fit to connect the EA to the ventilator circuit. An optional feature is a suctioning port, which allows care providers to suction patients without disconnecting the patient from the ventilator. However, this port is rarely used by care providers because of its small size. The two ends also swivel to allow optimal positioning of the ventilator circuit. The connection between the IC and EA is the most common point of failure due to secretions from the stoma loosening the friction fit. These disconnections may be harmful for the patient. The EA is typically replaced every 7-14 days.

The Shiley Tracheostomy Tube with Disposable IC (see, e.g., FIG. 5) is also a standard prior art device that is widely used. The Shiley Tracheostomy Tube has a list price of $76.65 and the Shiley Disposable IC has a list price of about $11.99 each. This IC is disposed of and replaced daily, while the tracheostomy tube (OC) is replaced every 4-8 weeks for inpatient use and 8-12 weeks for outpatient use. The two components feature a 15 mm snap-lock connector (clip mechanism). While the clip mechanism is designed for quick and safe disposal after a single use, care providers and patients attest that it is a common mistake to not clip fully. In addition, the force into the stoma that is necessary to make a proper connection is uncomfortable to the patients and can lead to stoma enlargement.

Figure 8:
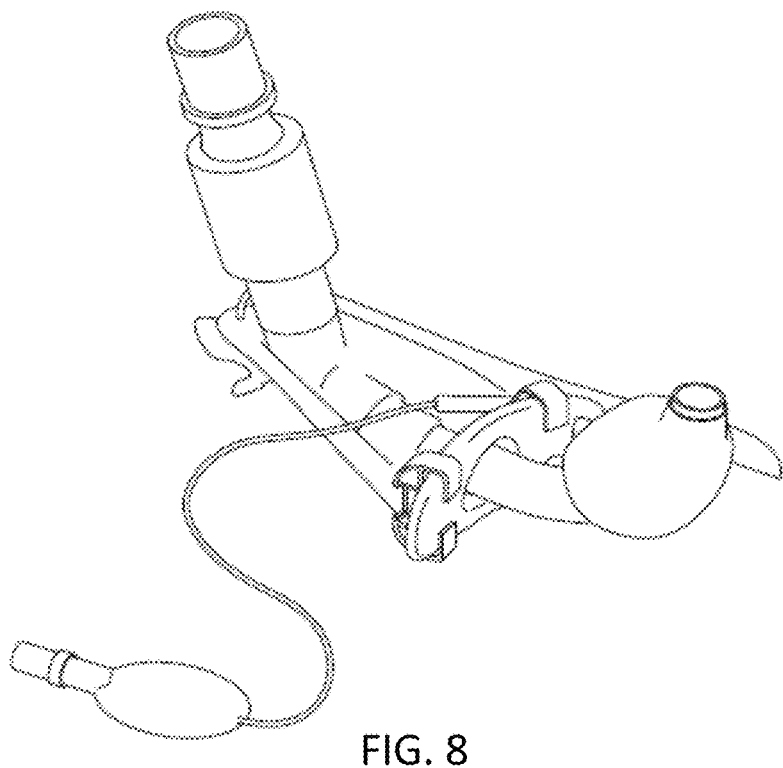
FIG. 8 illustrates one example of an anti-disconnect device as described herein, which may be referred to as a stronghold Anti-Disconnect Device.

The Stronghold Anti-Disconnect Device shown in FIG. 8 is a newer prior art device on the market to prevent disconnections between the IC and the EA. It involves a strap that connects to the faceplate of the tracheostomy tube and wraps around the back of the EA. However, due to its connection to the tracheostomy tube, the device could make tracheostomy tube dislodgements more likely, which may be extremely dangerous for the patient. Additionally, the device prevents fast connection and disconnection that would be needed for suctioning.

After compiling background research and current problems with tracheostomy tube, we developed the following problem and need statements:

Problem: The respiratory circuit unintentionally disconnects too often, disrupting the patient's ability to breathe.

Need: Reduce the number of unintended airflow disruptions in the respiratory circuit.

This need was chosen to provide safety for tracheostomy patients with a mechanical ventilator. The additional problems the prototype needs to address are a more comfortable tracheal fixation device and minimization of pressure sores.

We designed, built, and tested a prototype to address the needs of ventilator dependent tracheostomy patients (e.g. tetraplegic patients) and care providers and completed a final report for our design. We also completed a preliminary hazard analysis to investigate current risks of our prototype.

In designing a next-gen trach tube, there is a conflicting need to make connections stronger, while allowing disconnections to be readily made when necessary. We did not want to increase the chance of trach tube dislodgement by increasing connection strength. Another constraint was being unable to test our device on a patient. The prototype described herein is configured to deliver oxygen to the patient's lungs by completing the pathway between the ventilator circuit and patient. This design may be used for vent-dependent patients with a tracheostomy.

From our research and interviews, primary and secondary requirements were generated for our design (Table 1). Primary requirements are necessary for a device that will address the aforementioned problems and need. Secondary requirements would add to the user experience of the device, but are not necessary for functionality.

Table 1 below is a summary of the primary and secondary requirements. A priority of 1 indicates a requirement that we will attempt evaluate met this term. A priority of 2 and a priority of 3 indicates a primary requirement and secondary requirement, respectively.

| Priority | Requirement | Parameter | Specification |
|---|---|---|---|
| | | PRIMARY DESIGN REQUIREMENTS | |
| 1 | Minimizes unintended disconnections | EA-IC connection strength | Connection strength ≥45 N tensile force under dry and lubricated conditions |
| | | IC-OC connection strength | Connection strength ≥45 N tensile force under dry and lubricated conditions |
| 1 | Minimizes trach tube dislodgement | Tracheostomy securement strength | ≥Strength of Dale and Shiley devices |
| 1 | Air pressure sensitivity | Ventilator alarm pressure range | Accept airflow: 0-50 ± 5 cmH$_2$O<br>Reject/relieve airflow ≥60 ± 5 cmH$_2$O |
| 1 | Portable | Vibration | Withstand acceleration ≥1.1 m/s$^2$ |
| | | Humidity | 30-60% |
| | | Temperature | 0-95° F. |
| | | Weight | ≤weight of current design (individual pieces or whole apparatus) |
| 1 | Compatible with current art | Diameter of connections | 15 ± 0.2 mm or 22 ± 0.2 mm |
| | | Force | >45 N for 1 min |
| 2 | Easy to use | Time of assembly | Assembled and disassembled in <1 min<br>Assembly time ≤ current design |
| | | Assembly errors | IC-OC errors ≤ current design<br>IC-EA errors < current design |
| | | Assembly Force | Assembly force <130 N. |
| 2 | Biocompatible | Skin irritation test | Average <0.4 |
| | | Delayed hypersensitivity | 0 |
| 2 | Comfortable | Survey | 4 out of 5 on a comfort test, compare to current device. |

-continued

| Priority | Requirement | Parameter | Specification |
|---|---|---|---|
|  |  | Force applied to neck | ≤current device |
|  |  | SECONDARY DESIGN REQUIREMENTS |  |
| 3 | Cost | Similar to current | ±25% current cost of part or whole |
| 3 | Recyclable | Efficient | >90% return of material post recycling |
|  |  | Effective | <$0.50/lb to recycle |
| 3 | Durable | Life cycle - IC | No device failure for >1 day |
|  |  | Life cycle - OC | No device failure for ≥3 months |
|  |  | Withstand air pressure | No device fracture at 0-80 cmH$_2$O |
| 3 | Translucent | Visual inspection | Yes/No |

Disconnections of the EA from the trach tube are a significant problem. In order to minimize this event the tensile strength of the EA-IC connection will be used as a parameter for quantification. The strength of this connection must be greater than or equal to 45 N as per ISO 5367; therefore, our device does not disconnect at forces lower than this. Due to the lubrication problem, we have determined the strength of connection for lubricated conditions must also be greater than or equal to 45N. Therefore, our specification for minimizing unintended disconnections is that the strength of connection must be greater than 45N for both dry and lubricated conditions.

Trach tube dislodgement limits oxygen delivery. To minimize the occurrence of this event, the tensile strength to pull out a trach tube will be used as a parameter. Due to the danger of this event, specific data about the forces and loading mechanisms involved in dislodgement is not readily available. Testing methods will be designed to simulate the tensile force for trach tube dislodgement. Additionally, if the connections are strengthened, the securement will need to be strengthened so that is does not become a new point of failure. Therefore, our specification is that our design requires a greater force to dislodge the trach tube than current Shiley trach tube and Dale fixation devices.

The current fixation device irritates the user's neck and can cause delayed hypersensitivity. Our device should not cause these problems. To test this requirement, an irritation test and a delayed hypersensitivity test performed per the ISO/AAMI 10993.10 standard is made. An average score of less than 0.4 on a 5 point scale would indicate no irritation occurs and scores of 0 indicate no hypersensitivity.

Excessively high pressure from the ventilator has the potential to cause lung damage, and our device may protect the patient from this. The ventilator alarm pressure range will be used as a parameter for how much pressure may be allowed through the ventilator circuit before relief or release. Our specification for this requirement was that our device accepts air pressure ranging from 0-50±5 cm H$_2$O and reject or relieve air pressure above 60±5 cm H$_2$O. This specification was derived according to our client's high pressure ventilator alarm setting at 65 cm H$_2$O.

Because some patients may be in a wheelchair, the next-gen apparatus may be portable and can be easily carried while withstanding the rigors and varying environments of frequent travel. Our design is able to withstand vibration from travel, varying temperatures and humidity, and be lightweight. According to the AAMI standard HE75:2009 our design is able to withstand an acceleration of at least 1.1 m/s$^2$ along with humidity values ranging from 30 to 60% for use in travel. For example, the temperature tolerance may be between 0-95° F. to accurately represent common environments. Lastly, the weight of the next-gen devices described herein may be less than or equal to the weight of the current device and may be easily carried on a wheelchair.

A device that can be quickly and correctly assembled may be necessary. For some patients, survival time without adequate air supply would be less than two minutes. Therefore, the ability for caregivers to assemble and re-attach the circuit should be less than that time. The device described herein may be assembled in less than one minute as this should still be within a safe range to prevent damage to the patient. Additionally, the device is able to be assembled correctly within that time as incorrect assembly could be detrimental to patient safety and cause disconnections later on. Finally, an AAMI standard for usability indicates that the average woman, such as a care provider, would be able to apply tensile forces of 130 N to disconnect the device during required disconnections. Therefore, the force to disassemble our device should not exceed 130 N in tension, otherwise a care providers may be unable to disconnect the device when necessary.

Outer diameters of connections of ventilator and tubing components are 22±0.2 mm or 15±0.2 mm. Our device would meet this specifications to ensure that our device is compatible with other circuit components patients would need to use. Other components may use a standard size friction fit, changing size of the connections would require changes in many components.

The current fixation (prior art) devices can cause irritation and create sores around the neck, and may cause a strangling sensation at times. Additionally, the current IC-OC clipping connection is very uncomfortable to the patient due to large force pushed against the neck. In order for our device to be comfortable, the force of assembly may be less than or equal to the current clip and friction fit design.

Mechanical ventilation produces a significant amount of medical waste from disposable parts that are typically thrown away or incinerated after use. The devices described herein may be recycled efficiently with more than a 90% return and inexpensively at a cost of less than 50 cents per pound of material recycled. This would reduce the amount of medical waste produced without being prohibitively expensive.

Typically, the IC is replaced daily, the EA replaced by care providers every 7-14 days, and the OC is replaced every 8-12 weeks for sanitary reasons and to prevent failure from prolonged use. Therefore, the IC, EA, and OC should be able to survive normal use for their entire lifespan. The next-gen trach tubes described herein may be able to withstand air pressure created by a mechanical ventilator to prevent any unintentional breaks in the ventilator circuit. According to an FDA guidance document for mechanical ventilators, each ventilator is able to supply up to 60 cm H$_2$O air pressure with an option for respiratory therapists to increase this air pressure to 80 cm H₂O in extreme scenarios. The devices described herein may withstand flow without fracture from 80 cm H₂O air pressure.

These devices may also be made translucent for visual inspection.

Next-Generation Trach Tube Overview

Exemplary "next-generation" tracheal tubes as described herein are shown in FIGS. 9-14. In general, these tracheal tubes 100 include an outer cannula (OC) 101, an inner cannula (IC) 110, an elbow adapter (EA) 120, and a pressure valve 130. Trach tube 100 consists of three major innovations to the current tracheal tube: the connection between the outer and inner cannula (IC 110 to OC 101 connection), the connection between the inner cannula and the elbow adapter (IC 110 to EA 120 connection), and a pressure release valve 120. In particular, we have found and describe herein a surprisingly better properties and comfort when the connection between the outer and inner cannula is a threaded connection, and when the connection between the inner cannula and elbow adapter is a BNC connection, and when a pressure value is included.

A threaded connection 102 between the inner cannula (IC 110) and outer cannula (OC 101) connection may provide increased confirmation of correct assembly and decreased pressure against the stoma during assembly. For the IC 110-EA 120 connection, a BNC type connection 112 may provide improved strength in the presence of secretions and ease of intended disconnect. The pressure release valve is intended to release excess inspiratory pressure when the ventilator pressure exceeds the safety threshold.

In general, the OC 101 and the IC 120 both possess arcuate bends that provide a natural path from the stoma down the patient's trachea. The OC and IC may be constructed of flexible, semi-flexible or rigid materials. The OC and the IC may be constructed of the same materials or may be constructed from different materials. Because the OC will come into contact with a patient's tracheal walls, having a pliable and softer material may cause less irritation to the patient's trachea.

Figure 9:
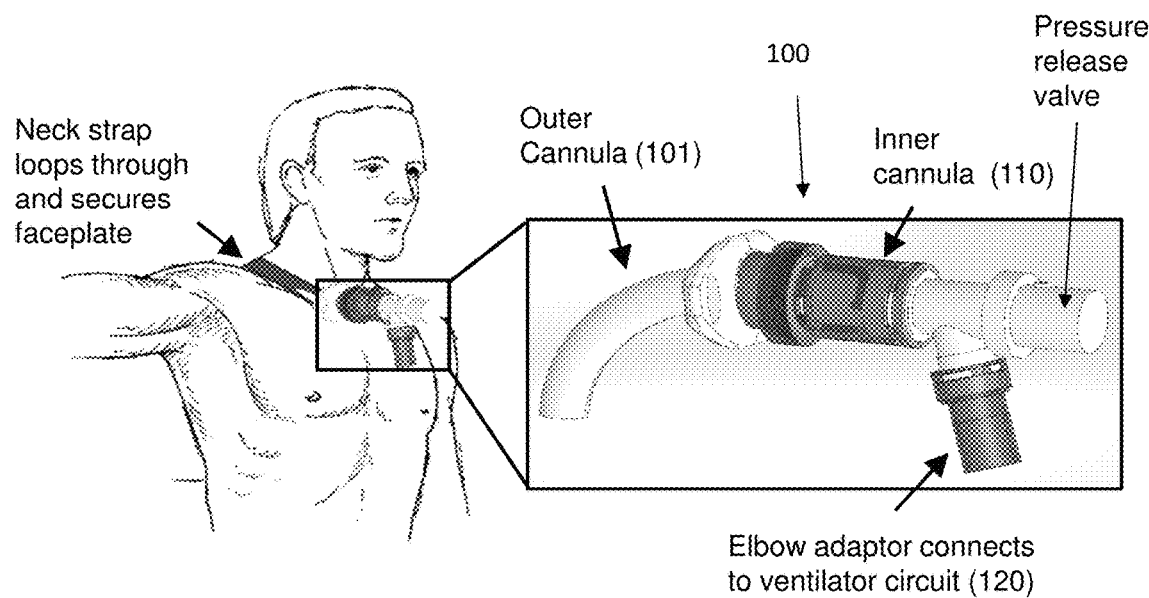
FIG. 9 illustrates an overall layout of the next-gen tracheal devices (shown configured for use as a tracheostomy tube) described herein.

The threaded 102 and BNC 112 connections will hold the IC 110-OC 101 and IC 110-EA 120 together, respectively. FIG. 9 shows an example of a layout diagram of where the assembled device will be operating. The distal end may be connected to the ventilator circuit allowing connection to the ventilator.

Figure 10:
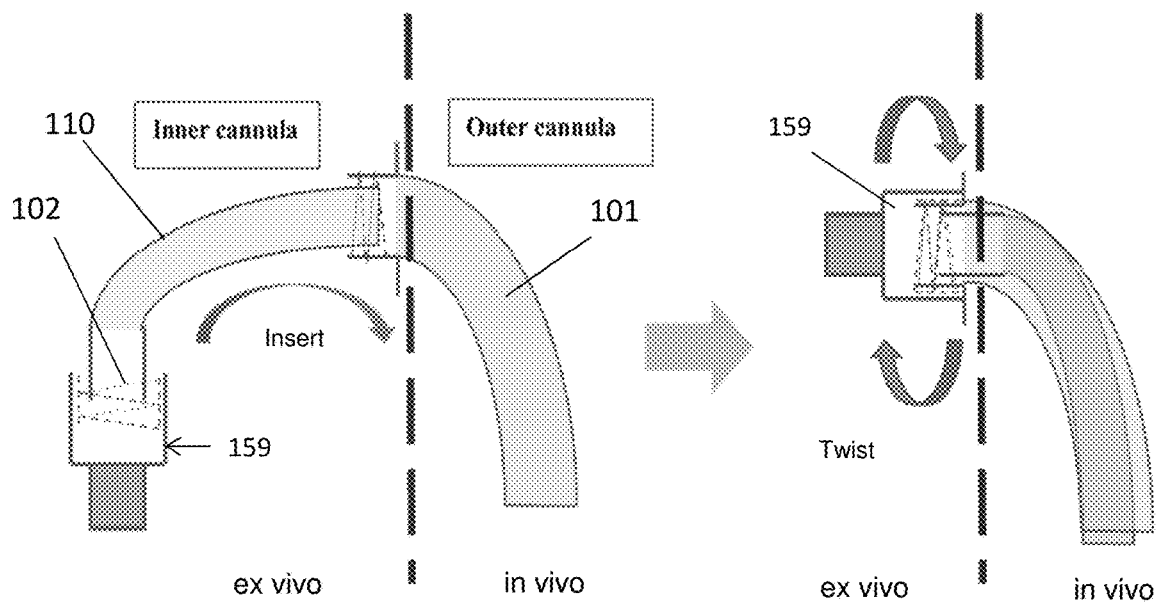
FIG. 10 illustrates the threaded connection layout for a portion of a tracheal tube as described herein (e.g., in which the ex vivo and in vivo portions are secured together by a threaded region).

The prior art clipping connection between the IC and OC in this example have been replaced with a threaded connection 102 (FIG. 10). Threads have proven in many applications to be strong and secure, and our design will address the current issues with ease of assembly and comfort. As mentioned in the background, the current clips are visually misleading and require a large force towards the patient's throat for complete connection, while threads would be easier to see and require less force on the stoma. The user could confirm correct connection when threads are no longer visible.

It must be noted that the twisting motion for the threaded assembly is slightly more complex than the pushing motion for the clip assembly, however we have found that the improvement in visual clarity and decreased force outweighs the increased complexity for this connection. Finally, the force for assembly is parallel to the throat's surface for the threaded connection, surprisingly reducing patient discomfort.

In general, there is a threaded connection between the inner and outer cannula. For example, the inner member may include a swiveling/rotating piece (e.g., end cap or end flange) that is configure to twist and/or rotate (e.g., relative to the body of the inner cannula, or it may be rotationally fixed relative to the body of the inner cannula). This cap or flange, which may be an inner cannula coupler such as shown in FIG. 10, may include internal threads or pins/projections for engaging with threads or pins/projections on an outer surface of the outer cannula, as shown in FIG. 10.

The threaded connection 102 may be made with a ridge on the IC 110 and a swivel piece that rotates around the ridge. Three total threads may be rotated about for the device to be assembled correctly; three threads may make the connection secure while also being easy to use. Threads may be located inside the swivel piece on the IC (I.D.=25 mm) and may rotate about threads on the outside of the OC 101 (e.g., O.D. approximately 22 mm). The swivel piece is external (e.g., approximately 200 µm diameter clearance) to the IC 110 and may twist without moving the IC 110 within the OC 101. The prototype OC is made of any appropriate biocompatible material. In the examples described herein, the OC is made of VeroWhitePlus (ObJet 3D printer rigid material), while the IC head and tail will are made of VeroWhitePlus and DM9795 (ObJet 3D printer flexible material) respectively. For the prototypes described herein, 3D printing was used to provide a fast, cost-effective fabrication method. Any other materials and/or fabrication methods may be used. In some examples, the connection between the IC and the OC may be a modified Luer lock type connection having connections inside a swivel piece on the IC and corresponding connections on the outside of the OC. In other examples, a swivel connection may be made between the IC and the OC using a series of protrusions (e.g. tabs, knobs) and corresponding apertures (e.g. slots, channels) where the connecting piece is able to swivel for connecting the IC and the OC at a desirable angle.

As mentioned, the connection between the EA and the IC may be a BNC mechanism 112 (FIG. 11). A BNC connection 112 may address the issues of common disconnections due to lubrication of the current design friction fit and poor intuitive usability due to users neglecting the twist step. A BNC connection 112 may have higher strength because the pin may provide extra support and the majority of the friction fit will be retained. The fit may be assembled correctly more frequently than the current, because the user will be forced to twist the pin through the channel as opposed to the friction fit where twisting motion is not clearly indicated. While this twisting motion is slightly more complex due to the channel, we have found that the complexity of the twisting motion is outweighed by the fact that the twisting is performed consistently as opposed to the current friction fit. Furthermore, a notch at the end of the channel may indicate to user the correct assembly (via tactile feedback), as well as helping to prevent unintended disconnections. As explained earlier, friction fits more distal in the ventilator circuit may be retained as they are less exposed to secretions.

A BNC connection 112 may be comprised of two pins 114 on the IC 110 (O.D. with pins=approximately 18 mm) and two channels 122 on the EA 120. To allow for ease of use, each channel 122 may allow the pin 114 to move, e.g., approximately 5 mm directly forward before beginning the twisting motion inside of the channel. Additionally, the channels may be curved with a 90° arc for a smooth, easy twisting motion. The EA and the IC may be fabricated from any appropriate material; for the prototypes, the EA and IC were fabricated using Objet 3D printers, so each component (IC pins and EA swivel with channels) were made of VeroWhitePlus.

A current catheter port at the back of the EA 120 may be included; alternatively or additionally, the apparatus may include a pressure release valve 130, as mentioned above. Pressure release valve 130 will help mitigate concerns of damage from high ventilator pressure by allowing air to escape at excessively high pressure (see, e.g., FIGS. 12A and 12B). This will be a novel feature for the EA 120 to protect patients.

In general a pressure release valve (which may also be referred to as a pressure relief valve) may be included that can be provided with a variety of pressure release settings, depending on the patient need. For example, the apparatus may include a pressure release valve that is configured to release pressure at or above one of 25 cm $H_2O$, 30 cm $H_2O$, 40 cm $H_2O$, 50 cm $H_2O$, 60 cm $H_2O$, 65 cm $H_2O$, 70 cm $H_2O$, 80 cm $H_2O$, 90 cm $H_2O$, 100 cm $H_2O$, 110 cm $H_2O$, 120 cm $H_2O$, etc. In some variations the pressure release threshold may be selectable and/or adjustable. For example, the valve may have more than one pressure setting triggering pressure release. The pressure release valve may be set (e.g., by a user) to select different pressure thresholds above which pressure is released. For example, if the pressure release valve includes a spring element, the spring can be pre-set to achieve desired pressure release requirements. The pressure release valve may include a control (e.g., knob, dial, switch, etc.) allowing selection of different pressure release settings (e.g., one or more of: approximately 40 cm $H_2O$, approximately 45 cm $H_2O$, approximately 50 cm $H_2O$, approximately 55 cm cm $H_2O$, approximately 60 cm $H_2O$, approximately 65 cm $H_2O$, approximately 70 cm $H_2O$, etc.). The control may be lockable into a particular setting (e.g., it may include a lock and lock release such as a button that can be toggled to allow it to be changed).

Figure 12B:
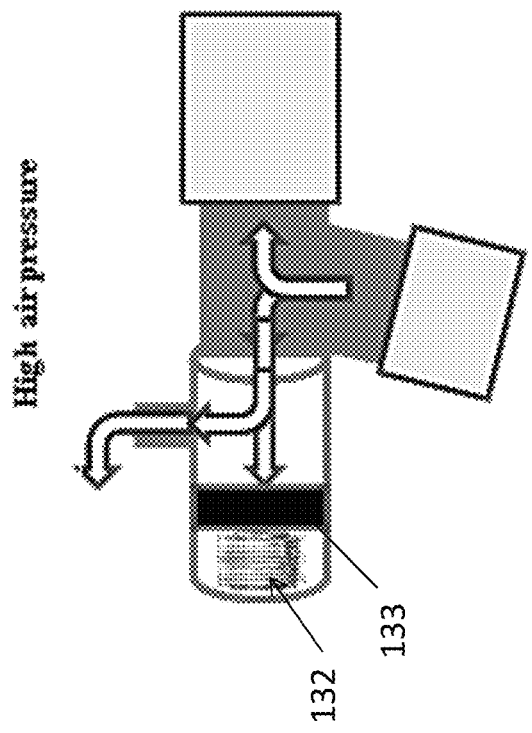
FIGS. 12A and 12B illustrates a pressure release valve response at different pressure levels.
Figure 12A:
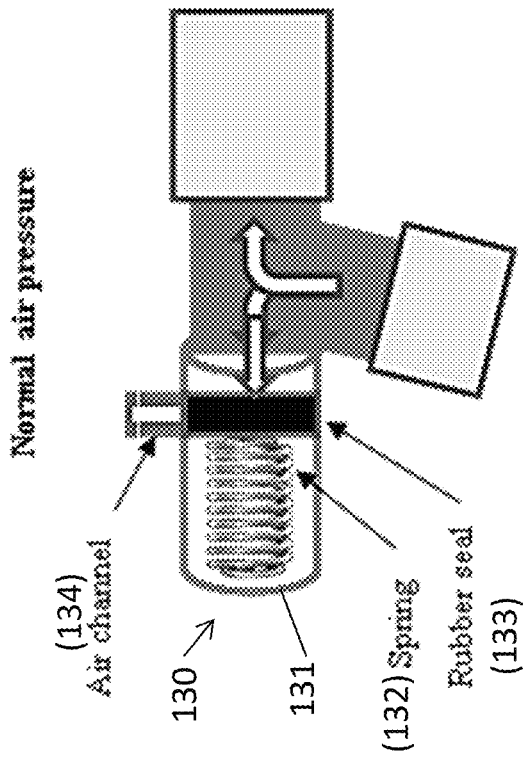

The pressure valve 130 may consist of a casing 131, a spring 132, and a ridge containing a rubber seal 133. The seal 133 may be pushed back at high air pressure, and may compress the spring 132, and allow air to escape through a hole 134 in the valve casing 131 as illustrated in FIG. 12B. According to some variations, the valve may be configured to open at pressures above about 65 cm $H_2O$. A compression distance of about 5.14 mm and a spring constant of 0.19 N/mm were chosen in one example according to calculations of the functional and mechanical needs, and availability of commercial springs.

The pressure valve casing 131 may contain a hole 134 (e.g., having an approximately 2 mm diameter) at a distance of about 5.14 mm from the edge of the pressure valve 130 connecting to the EA 120. The pressure valve 130 may be connected to the EA 120 by a threaded mechanism similar to the proposed IC 110-OC 101 threaded connection 135. This casing may be fabricated from any appropriate material (the prototype described and shown in the figures was formed by an ObJet printer and made of VeroWhitePlus). The chosen spring (e.g., constant=about 0.19 N/mm, free length=about 19.05 mm) may be made of stainless steel. A custom-ordered spring may be used in accordance with optimal dimensions of the casing. The rubber seal (O.D.=about 14 mm) may snugly fit over the ridge piece and be placed on top of the spring prior to attachment to the EA. In this example, these seals (Nitrile rubber) may be ordered from Amico and the ridge piece will be fabricated by an ObJet printer and made of VeroWhitePlus in our prototype.

Figure 1:
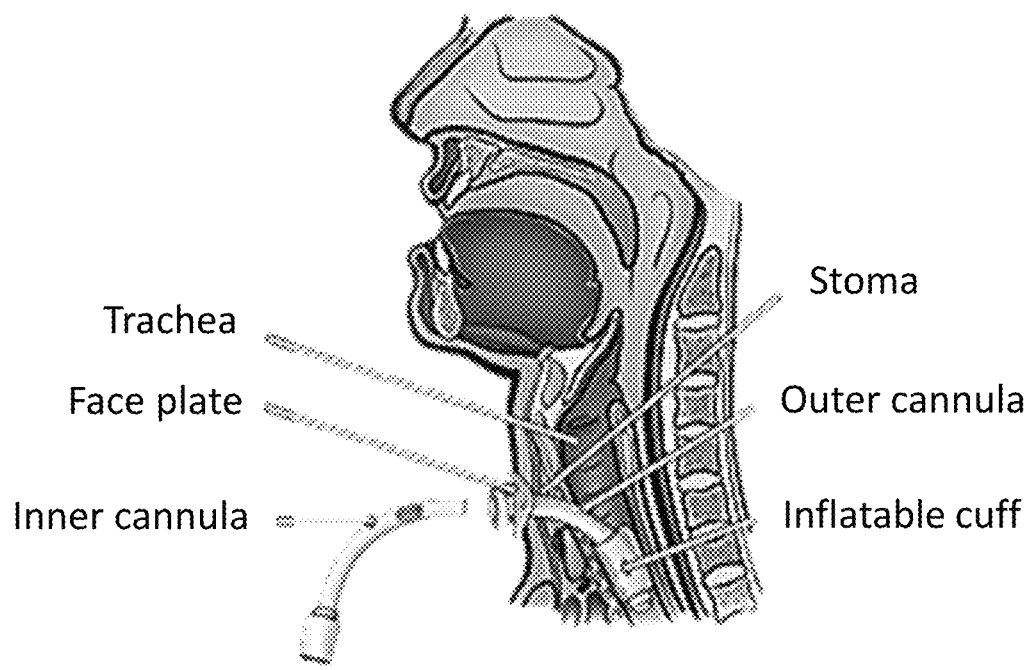
FIG. 1 illustrates typical tracheal tube (shown as a tracheotomy tube) components.

As can be seen, the trach tube may also include an inflatable cuff, (such as shown in the prior art of FIGS. 1 and 4). An inflatable cuff may be advantageous because it may aid with maintaining position of the trach tube once a desirable position has been obtained. Typically a cuff may be disposed on the distal end of the OC having an inflation and deflation port integrated into the IC and OC assembly. One drawback of having a cuff is that moisture may collect around the cuff if the patient is consistently in a reclined position. Thus, in certain instances, gentle suction may be used periodically with the aid of channels or lumen that terminate at various positions along the trach tube and that have corresponding ports that allow for attachment to a suctioning device at the proximal end of the trach tube. The suctioning of moisture along the trach tube may be performed manually or periodically imitated by controls on the ventilator.

Any of the devices described herein may also include a speech valve. For example, in the instance where the trach tube includes a cuff, a speech valve may also be included. A speech valve may be disposed at the end of the trach tube to allow a patient to speak more easily. The speech valve is typically a one-way valve that allows inhalation to pass through the IC but forces air from exhalation to pass through a patient's regular respiratory organs (subglottic trachea, larynx, pharynx, mouth, and nasal passages) and allow for vibration of the patient's vocal cords and ability to speak. In some examples a speech valve may be a flapper valve. Any appropriate speech valve (and particularly those for use with tracheostomies) may be used, for example, see U.S. Pat. Nos. 6,588,428, 5,392,775, US20120103342, each of which is herein incorporated by reference in its entirety.

In certain instances, a patient may require a trach tube for an extended period of time. Surfaces exposed to a warm and moist environment are more apt to foster microbial growth over time. This may be detrimental to those already may be in fragile state. In some instances, it may be advantageous to coat portions of the trach tube with anti-microbial agents. Anti-microbial agents may include but not limited to sulfadiazine compounds, chlorhexidine compounds, silver coatings, gentian violet, and so forth. In some other variations, the internal walls of the IC or OC may be coated with hydrophobic material in order to minimize moisture collection within these tubes.

The trach tube may further include a faceplate. The faceplate may be situated at the interface between the patient's skin and the connection point between the IC and the OC. It is desirable for the faceplate to be constructed of a soft, cushioning material on the surface that contacts the patient's skin. In some instances, it would be desirable to have a low profile faceplate for more visually appeal.

Device Operation

To insert the OC 101 into the trachea, the user may insert the tail of the cannula into the stoma, following the curvature of the tail down into the trachea. The OC 101 would be secured by looping Velcro strips through holes in the faceplate and securing them on a trach tube holder around the patient's neck. To connect the IC 110 to the OC 101, a user may insert the IC 110 into the OC 101 until the threads of each part meet as shown in FIG. 10. The user may then twist the cannula screw clockwise onto the OC threads until the threads can no longer be seen (notifying the user of correct assembly). To connect the IC 110 to the EA 120, the user may slip the pins 114 on the IC 110 into the channel 122 of the EA 120 as shown in FIG. 11. The user may then push and twist the EA 120 clockwise onto the IC 110 in one motion until the pins 114 of the IC 110 fit into the notch at the end of the EA channel 122. Finally, the distal end of the EA may be connected to the rest of the ventilator circuit with a standard friction fit.

To disconnect the EA 120 from the IC 110, the user may push the IC 110 and EA 120 together slightly to allow the IC pin 114 to move out of the notch and into the channel 122. The user may then pull and twist the EA 120 counterclockwise to free the pins from the channel. To disconnect the IC 110 from the OC 101, the user may twist the cannula screw counterclockwise until the threads no longer touch. Then the IC 110 may then be pulled out of the OC 101. After disconnection, it is recommended that the user discard the IC 110 and replace it with a new, sterile device. Alternatively, if the OC were being changed, it may be pulled out of the trachea, following the curvature of the OC tail and immediately replaced with a new OC to allow continued ventilation.

A preliminary hazard risk analysis (PHA) was conducted for each design component to understand the possible risks associated with our design and to mitigate these risks prior to prototyping. The top three hazards for the connections identified were threaded connection failure, improper threaded connection, and BNC connection failure.

We completed a Design Failure Mode and Effect Analysis (DFMEA) for our completed prototype after validation and verification testing. RPN values were calculated by taking the product of the severity of the harm, the occurrence of the event, and the ease of detection. The guide for ranking is shown in Table 2.

TABLE 2

Guide for the rankings of all DFMEA values

| Measure | Range | Ranking |
| --- | --- | --- |
| Severity (S) | 1 to 10 | 1 = harmless |
| | | 10 = catastrophic |
| Occurrence (O) | 1 to 10 | 1 = never |
| | | 10 = always |

TABLE 2-continued

Guide for the rankings of all DFMEA values

| Measure | Range | Ranking |
| --- | --- | --- |
| Detection (D) | 1 to 10 | 1 = easy |
| | | 10 = impossible |
| RPN = S * O * D | 1 to 1000 | (RPN < 100) = broadly accepted |
| | | (100 ≤ RPN < 343) = ALARP |
| | | (343 ≤ RPM < 1000) = intolerable |

Events that resulted in a RPN value within the as low as reasonably practicable region (ALARP) were addressed with a recommended action. A summary of the DFMEA may be found in Table 3.

TABLE 3

DFMEA Summary

| Component | Failure mode | Failure mechanism | RPN = S * O * D | Recommended action |
| --- | --- | --- | --- | --- |
| Threaded connection | Improper connections | Insufficient twist of threads | 105 = 7 * 3 * 5 | Make cannula screw translucent & color inner threads to improve detection |
| BNC connection | Improper connection | Notch failure | 120 = 8 * 5 * 3 | Testing with chance of disconnection through normal joint movement & modify angle accordingly |
| Pressure release valve | Pressure release failure | Seal defect | 120 = 6 * 10 * 2 | Reevaluate material of seal and/or the method of sealing |
| Pressure release valve | Pressure release failure | Secretion hardening | 108 = 6 * 6 * 3 | Manufacture EA and pressure valve as translucent components |

The required compression distance, spring constant, and casing size of the pressure valve was calculated in order to design an effective system. The first parameter required for springs was that the outer diameter fit within the inner diameter of the pressure valve (14 mm). An ideal compression distance of 2-5 mm was determined in order to not create an excessively long pressure valve casing at the back of the EA. The force on the pressure ridge from 65 cm $H_2O$ (O.D.=14 mm) was calculated to be 0.98 N. From these parameters a spring from Fastenal was chosen with a free length of 19.05 mm and a spring constant of 0.19 N/mm. This spring would require a compression distance of 5.14 mm before the valve is completely open, so the casing was designed accordingly.

Figure 14A:
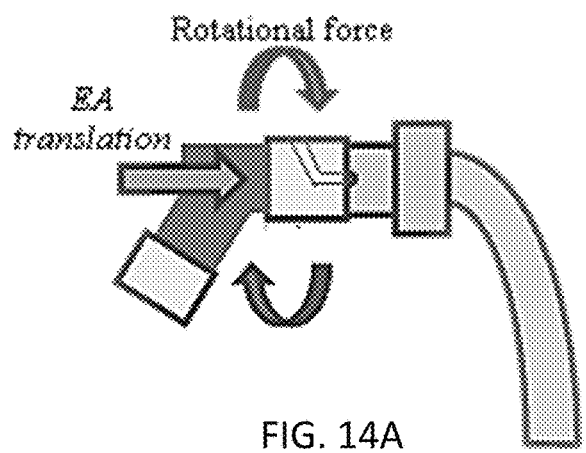
FIGS. 14A and 14B show a force diagram comparison between a BNC (left) connection and friction fit (right) connection.
Figure 14B:
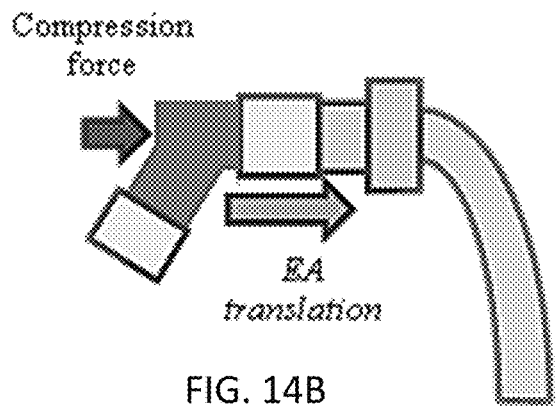

Force diagrams for the assembly of the friction, clip, threaded, and BNC fits were created in order to understand the force at the stoma experienced by the patient. FIGS. 13A and 13B compare a threaded and a clip connection. FIG. 14 compares the BNC and friction fit connection. These showed that the friction and clip connections require a direct translational force into the stoma, whereas threaded and BNC fits require a rotational force that results in translational motion towards the stoma. Actual forces associated with these analyses were measured with the force on stoma verification test.

Verification and Validation

The purpose of verification tests is to ensure that the device meets the design requirements described above. Diameters of the prototype apparatus should match the diameters for friction fits currently used. The force of assembly experienced by the patient should be small enough to not cause damage. Finally, both fits need to be able to withstand 45 N of force to prevent frequent disconnection.

The purpose of the validation methods is to ensure the needs of the patient are met and the device meets its intended use. The prototype needs to have fewer errors in assembly than the current device and make unintended disconnections less likely. The pressure valve may have proper pressure sensitivity such that air is released only at high pressures. The prototype may be easily transported for use in patient environments. Durability is important so the device may be configured so as not to fail before the end of its intended lifespan.

Table 4 below summarizes the results of this testing. The prototype met all tested specifications except for compatibility with current art, weight, and all pressure valve specifications.

The statistical significance of the collected data was determined using the SPSS Statistics Version 22 from IBM and Microsoft Excel 2011 with a significance level of 0.05.

TABLE 4

Summary of the results of each test performed

| Requirement | Specification | Test Name | Success Criteria | Results | Success |
|---|---|---|---|---|---|
| Verification | | | | | |
| Minimizes Unintended Disconnections | Withstand tensile force >45 N for 1 minute under dry and lubricated conditions | Dry Constant Force Test | No disconnection under dry conditions with tensile force of 50 N for 2 min | No disconnections under dry conditions | Yes |
| | | Lubricated Constant Force Test | No disconnection under lubricated conditions with tensile force of 50 N for 2 min | No disconnections under lubricated conditions | Yes |
| Compatible with Current Art | Diameter = 15 ± 0.2 mm or 22 ± 0.2 mm | Dimension compatibility | Successful connection | EA: 15.20 mm IC: 18.33 mm | No: proposed BNC-friction adaptor |
| Comfortable | ≤force into stoma for connection of current device (EA-IC & IC-OC) | Force on Stoma | ≤force into stoma for connection of current device (EA-IC & IC-OC) | Not Performed | N/A |
| Validation | | | | | |
| Air Pressure Tolerance | Accept airflow: 0-50 ± 5 cmH$_2$O Reject/relieve airflow: 60 ± 5 cmH$_2$O | Air Pressure Sensitivity | 0 activations ≤40 cmH$_2$O Increased activation at 50 cmH$_2$O compared to 60 cmH$_2$O | Air leakage every trial | No |
| Portable | Withstand acceleration ≥1.1 m/s$^2$ | Movement simulation | <1 average disconnection while in moving vehicle | No disconnection across all trials | Yes |
| | ≤weight of current design (28.5 grams) | Weight | ≤weight of current design (28.5 grams) | Current: 28.45 g Prototype: 42.84 g | No: proposed specification change |
| | 30-60% | Humidity Tolerance | No degradation within range | Not Performed | N/A |
| | 0-95° F. | Temperature Tolerance | No deformation within this temperature range | Not performed | N/A |
| Easy to Use | Disassembled and assembled in <1 min | Usability simulation: trained users | Disassembled and assembled in <1 min | Prototype: 15.75 ± 2.76 s <<60 s | Yes |
| | Time of assembly of prototype ≤ current design | Usability simulation: untrained users | BNC time of assembly of prototype ≤ current design | Current: 4.86 ± 1.04 s Prototype: 5.20 ± 1.06 s Not significant (p = 0.365) | Yes |
| | | Usability simulation: | Threaded time of assembly of | Current: 4.89 ± 1.47 s | Yes |

TABLE 4-continued

Summary of the results of each test performed

| Requirement | Specification | Test Name | Success Criteria | Results | Success |
|---|---|---|---|---|---|
| | | untrained users | prototype ≤ current design | Prototype: 6.24 ± 3.03 s Not significant (p = 0.846) | |
| | User can assemble device correctly with less errors than current design | Usability simulation: untrained users | BNC number of errors assembling prototype < current | Current: 3 ± 0.00 errors Prototype: 0.14 ± 0.35 errors | Yes |
| | | Usability simulation: untrained users | Threaded number of errors assembling prototype ≤ current | Current: 1.14 ± 1.25 errors Prototype: 1.86 ± 1.13 errors Not significant (p = 0.782) | Yes: must ensure proper user training on threading |
| Durability | 7-14 days | Durability: normal and high pressures (50:50) | Function without failure for >200 breathing cycles | Not Performed | N/A |

Dry Constant Force Test

This test determined if unlubricated BNC and threaded connections could tolerate sustained tensile forces in accordance with ISO 5367 to minimize the amount of disconnections. These tensile forces may be experienced during transportation when tubing can easily catch on people's arms or railings. Our specification is that the IC-EA and IC-OC connection is able to withstand a tensile force greater than or equal to 45 N for one minute.

Figure 15:
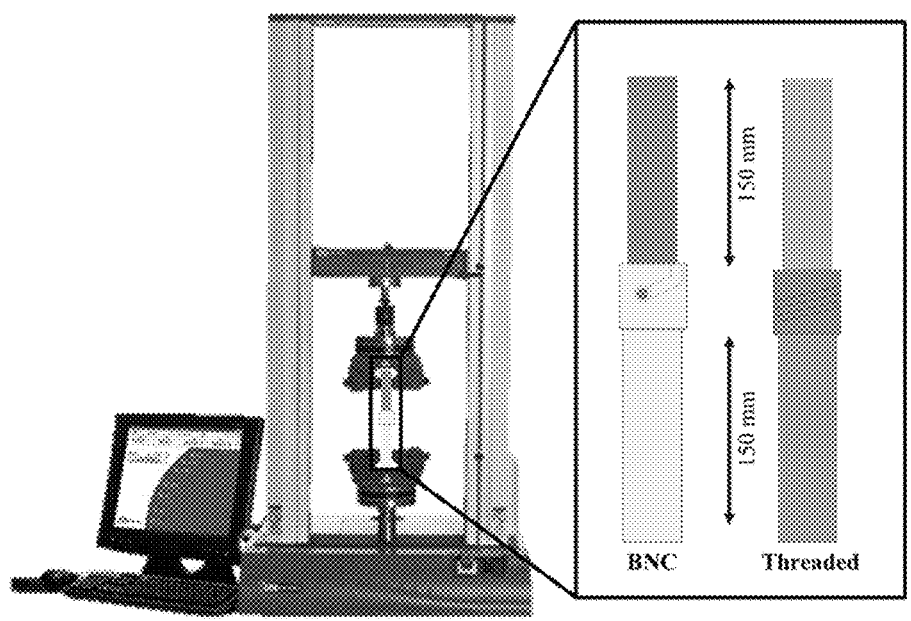
FIG. 15 illustrates one example of an experimental set-up for testing the apparatuses described herein, showing testing of BNC vs. threaded connectors.

BNC and threaded connections were assembled correctly prior to testing. The connection was placed in the upper and lower clamps of the Instron material testing machine 150 mm from each clamp as per ISO 5367 (FIG. 15). The Instron was run in accordance with ISO 5367 with increasing extension at a rate of 50.5 mm/min until 50 N of force was reached, and then held at 50 N for 2 minutes. Any visible disconnection or slipping of the connection was noted as described by ISO 5367. The Instron output displacement and force during testing. This test was completed on four BNC and four threaded connections.

Success was determined by the ability of the connections to successfully withstand a tensile force of 50 N for 2 minutes in dry conditions without slipping or disconnection.

Both BNC and threaded connections withstood a load of 50 N for 2 minutes in dry conditions, meeting our specification.

Figure 16:
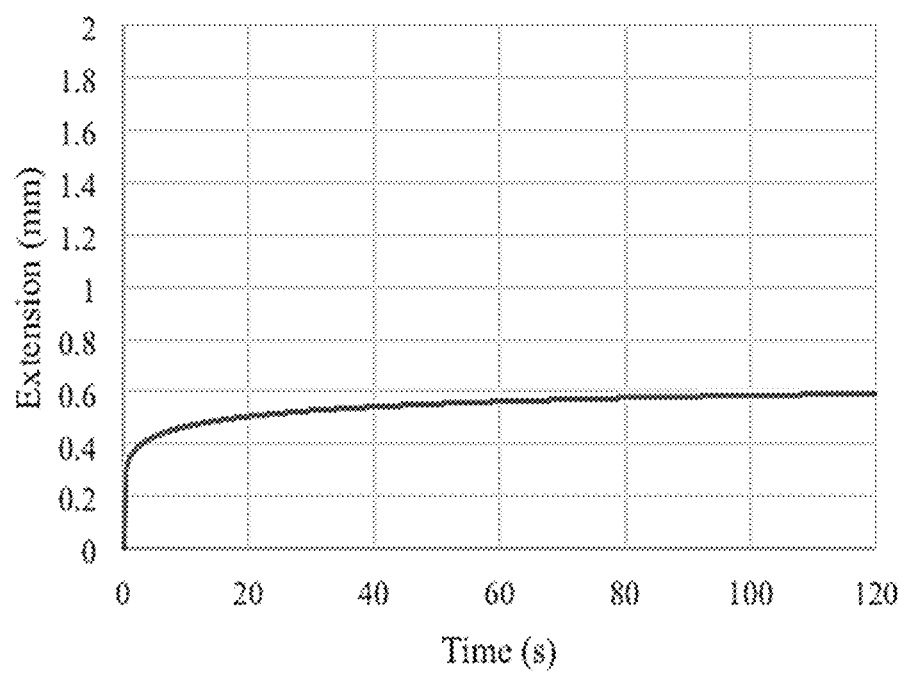
FIG. 16 is a representative graph of the extension over time (mm/s) of a threaded connection under constant force testing. Responses in dry and lubricated conditions were identical.
Figure 17:
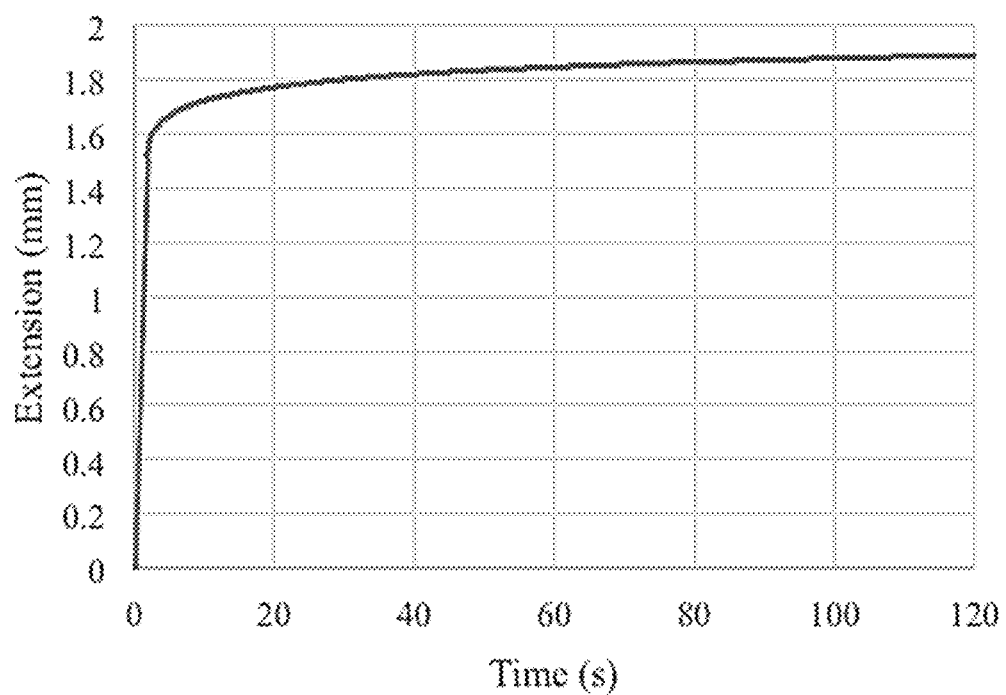
FIG. 17 is a representative graph of the extension over time (mm/s) of a BNC connection under constant force testing.

No disconnections, large movements, or plastic deformations were noted across any trials. Representative graphs can be seen for both threaded connection in FIG. 16 and BNC connections in FIG. 17. While small deformation was seen within the graphed data, % elongation for plastic deformation and significant deformation (defined by ISO 5367) was not observed during testing. We were limited to the use of VeroWhitePlus material during testing, but our proposed final material, e.g., PVC, would have similar tensile strength (VeroWhitePlus: 55-65 MPa, Rigid PVC: 35-60 MPa). Therefore, it is likely our final device would be able to withstand more than 45±2 N of tensile force for 1 minute.

Lubricated Constant Force Test

The purpose of this test was to determine if lubricated BNC and threaded connections can tolerate sustained forces in accordance with ISO 5367 to minimize the amount of disconnections. Lubrication was tested because the patient's skin oils and airway secretions can lubricate the joint. Our specification is that the IC-EA connection is able to withstand a tensile force greater than or equal to 45 N for one minute. This was assessed by a constant force test of the connections at 50 N for two minutes.

To accurately mimic patient conditions, airway secretions may be modeled by locust bean gum/borax mucus simulant shown to mimic the viscosity and elasticity of natural mucus. The end of the connections were submerged in lubricant and assembled as noted for the dry testing. The connection was tested using the same protocols as for dry conditions. This test was completed using the same connection pieces as mentioned prior.

Success is determined by the ability of the lubricated connection to withstand 50 N for 2 minutes without slipping or disconnection.

Lubricated BNC and threaded connections withstood a load of 50 N for 2 minutes, meeting our specification. No disconnections, large movements, or plastic deformations were noted across any trials. Observed outcomes were very similar to those in dry conditions, so we drew the same conclusions.

Compatible with Current Art

The purpose of this test was to determine whether our design was compatible with the current trach tube, ventilator, and ventilator circuit components. Connection with compatible diameters (e.g., about 15 mm and 22 mm) to the current design is a primary requirement. It would allow users to connect old equipment to the new equipment and still have proper functionality. Emergencies may occur and the old device may need to be connected, so we want to ensure patient safety.

To test the compatibility, we measured the outer diameter of the lower adaptor swivel on the EA along with the outer diameter of the IC (including the pins), as these would be the two locations our equipment could interface with currently used devices. The diameters of the EA and OC our prototype were measured by calipers.

Success will be determined by the prototype's ability to have a diameter of 15±0.2 mm for both the lower swivel and IC outer diameter.

The diameter of the EA connector to the breathing circuit was within 15.2 mm, but the connection from the IC to the EA was not within our specification. This is because the IC prototype included two BNC pins on the side, leading to a larger total diameter (as shown in FIGS. 18A and 18B, for example). However, the diameter without pins is 15.2 mm, indicating compatibility for friction between the EA and IC. We were limited to the use of calipers with 0.1 mm increments for measuring the diameter.

Force at Stoma

The purpose of this test was to determine if the prototype IC-OC connection can be made with less force on the stoma than the current device to prevent tissue damage and ensure patient comfort. A principle specification of our prototype is the force applied to the stoma during connection is less than or equal to the force of the current design. We want to ensure the patient is not injured by proper device use. The current design requires users to push into the patient's throat, which can be painful.

To test this, the proximal component of the connection may be fixed to a dynamometer (Vernier Dual-Range Force Gauge) (see, e.g., FIG. 19) and then the force over time of connecting the distal piece of both the BNC and threaded connections to their respective proximal pieces may be measured. From the graph the maximum force applied may be measured and we may calculate the total force applied. To get the total force, the curve with respect to time may be integrated. The mean and standard deviations may be determined for the maximum force and total force applied for the threaded and BNC connections, and these would be compared against the standard friction fit and clip mechanism, respectively (n=5 each). Two-tailed independent t-tests would be used for comparisons, and the means and standard deviations plotted in a bar graph.

The prototype apparatus may be determined as successfully comfortable if the prototype requires similar or significantly less force for assembly. A limitation of this testing method is the neglect of other aspects of the device that would complicate the force transfer between the connection and the stoma. To justify this, it may be assumed that the force for connection at either connection is directly translated to the stoma.

Acceleration

The purpose of this test was to determine if the prototype could withstand accelerations commonly experienced by patients. Patients travel and experience different environments, requiring a portable device. A critical specification for our prototype included being able to withstand accelerations greater than or equal to 1.1 m/s$^2$, similar to accelerations experienced during driving.

Figure 20:
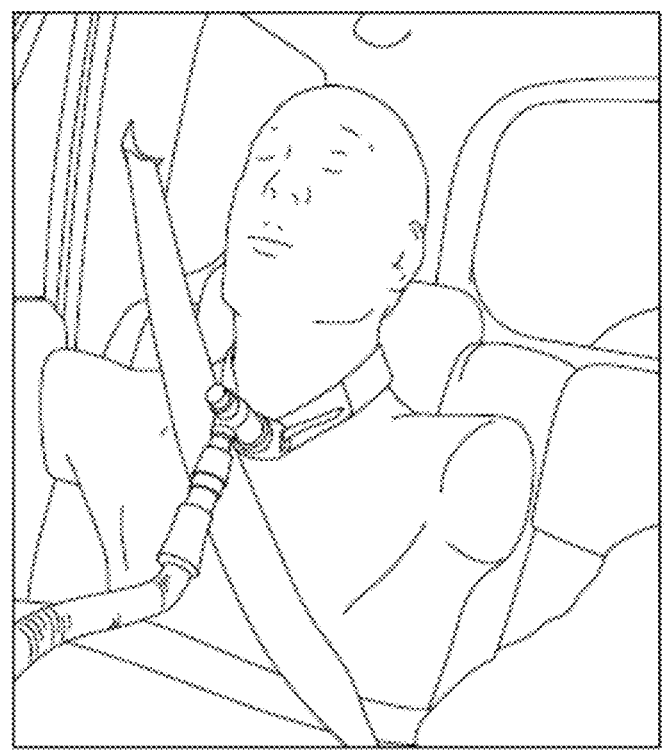
FIG. 20 illustrates one example of an acceleration testing dummy (in a car) for testing the devices (shown configured for use as a tracheostomy tube device) described herein.

To simulate quick movements for the acceleration test, a trach dummy with our prototype attached was secured in the backseat of a team member's car while driving (FIG. 20). The accelerations experienced by driving were much larger than 1.1 m/s$^2$ (25 mph to stop in four seconds=2.8 m/s$^2$) and accurately simulated unpredictable forces associated with mobile patients. Ventilator tubing was secured within the car at a fixed position, and an additional group member noted any disconnections that occurred in the tracheostomy tube during the drive.

An average of less than one disconnection among all trials was used as the success criteria for the acceleration test. We found that our prototype is able to accommodate accelerations greater than 1.1 m/s$^2$, indicating that the components will not disconnect do to accelerations from normal driving. During our driving simulation, zero disconnections were recorded during all three trials, even as the acceleration greatly exceeded 1.1 m/s$^2$.

Weight

The purpose of this test was to determine if the weight of the prototype is comparable to the current design. The device will apply force to the stoma so it should be lightweight to prevent damage.

The weight of the current design and our prototype were measured three times using a scale and the mean weight was recorded.

Success was determined by our device having a similar or lower weight when compared to the current design.

Figure 21:
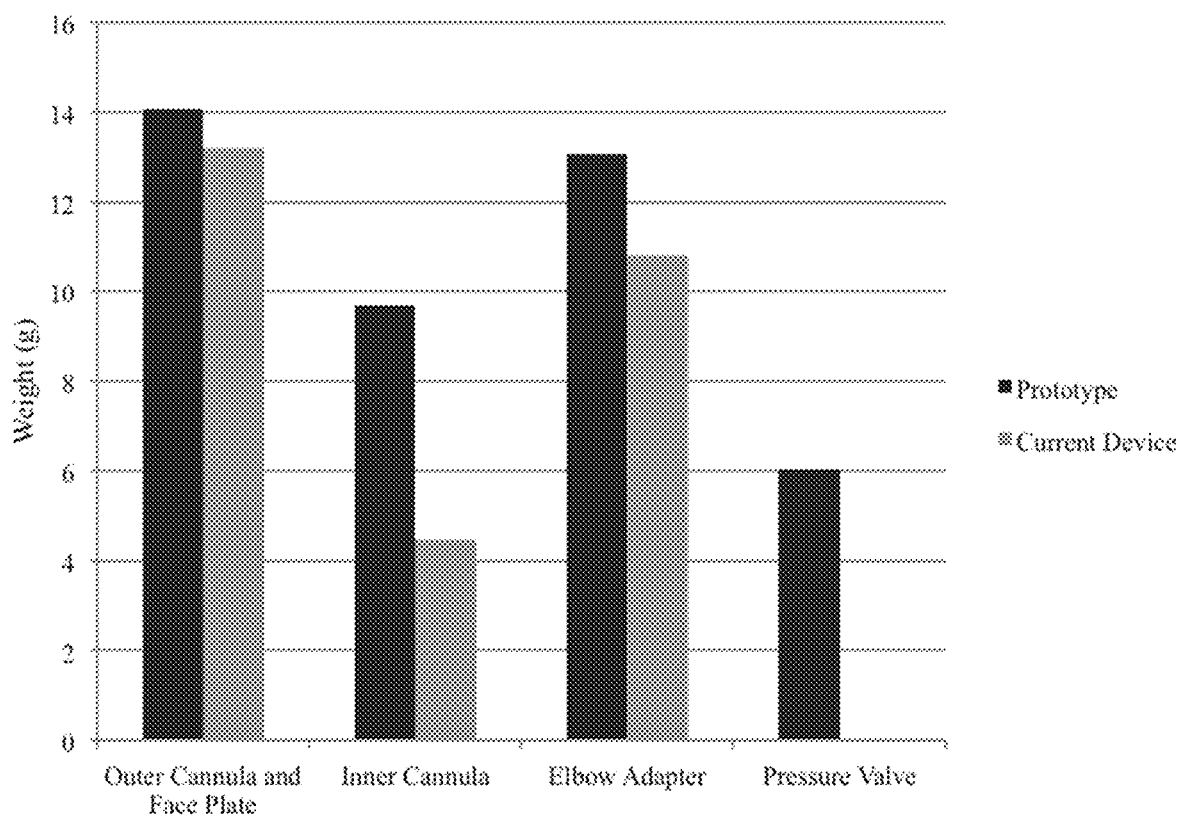
FIG. 21 is a graph showing a comparison between the currently available (prior art) tracheal tube devices and one variation of a next-gen tracheal tubes described herein ("prototype").
Figure 22:
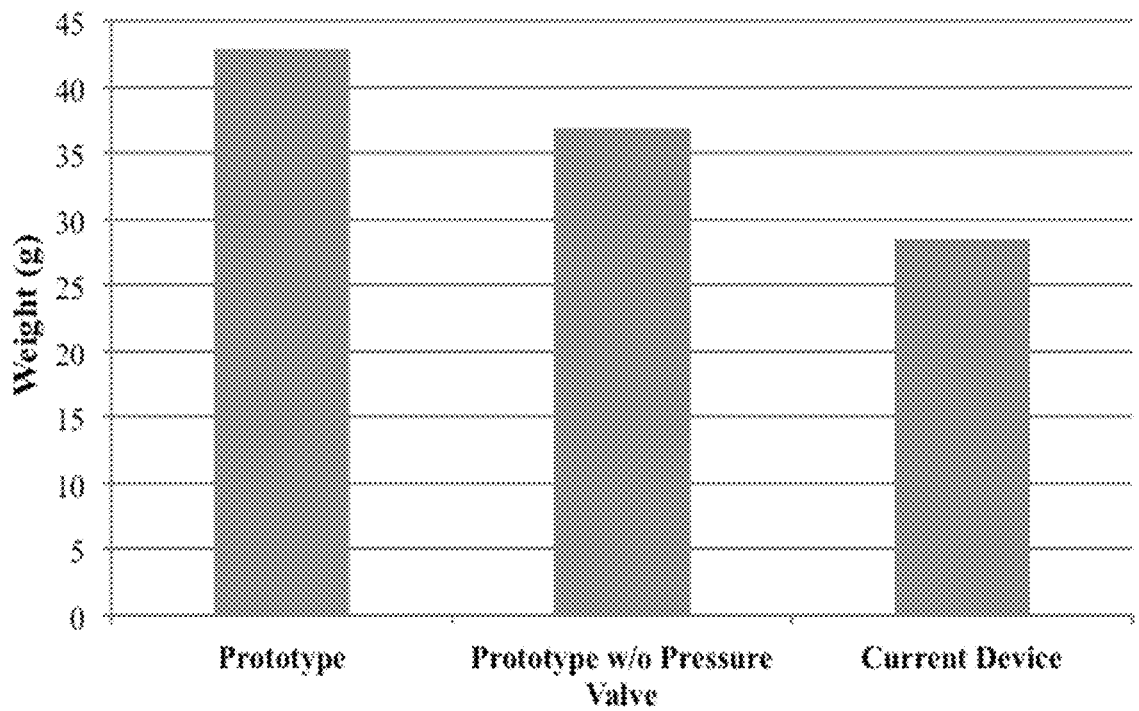
FIG. 22 is a graph showing a comparison between the total weights of the next-gen device (within and without pressure valve) and the prior art device.

All components of the prototype were heavier than comparable components of the current device (FIG. 21). The following groups were weighed: OC and face plate, IC, EA, and pressure valve. They were 6.58%, 117.43%, 20.91% and 50.58% heavier than the prior art device, respectively. The pressure valve is not present on the prior art device and therefore adds additional weight to the total weight of the prototype. Excluding the pressure valve weight, the total prototype weight was still greater than that of the prior art device by 29.36%. The total weight of each device can be seen in FIG. 22. The density of the material used in the current design (PVC) is greater than our prototype (VeroWhitePlus) indicating that our new design is still heavier than the prior art, even when adjusting for the material density. Aside from material choice, changes in dimensions to accommodate the 3D printing machine and excess wax supports from 3D printing added to the weight.

Usability: Untrained Users

The purpose of this test was to determine intuitiveness of threaded and BNC connections compared to the prior art device. Important specifications for our prototype include correct assembly in less than one minute and fewer assembly errors compared to the prior art devices. In emergency situations, a care provider may not be able to respond quickly enough and an untrained user may need to make the connections. It is crucial that the device is easy to use because it means more correct assemblies, which lead to fewer connection failures.

Figure 23:
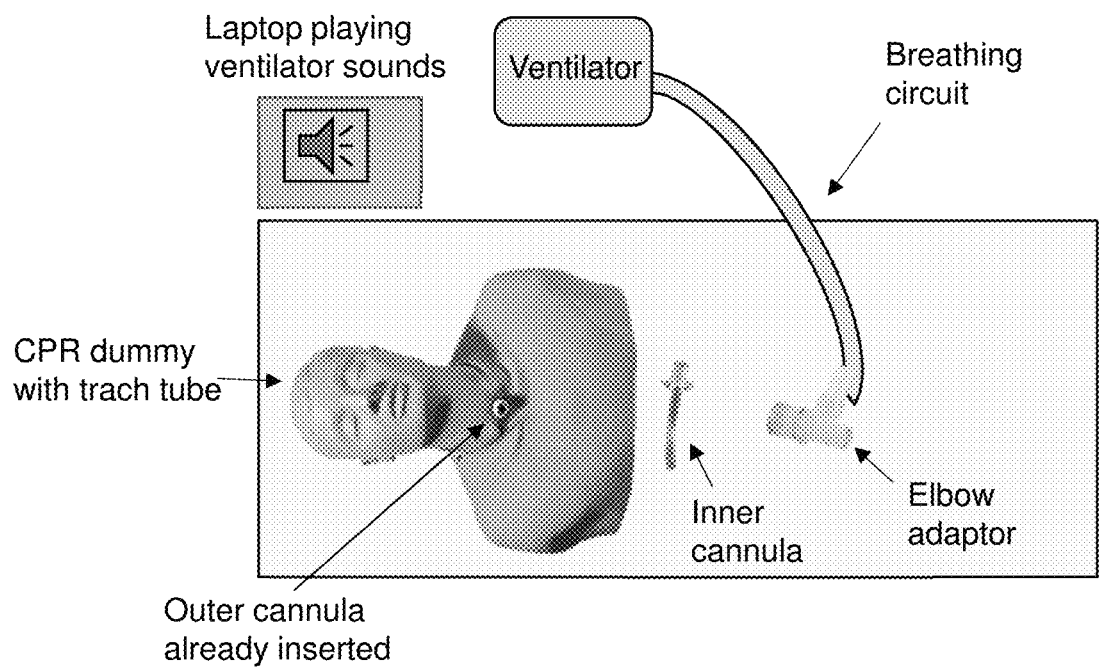
FIG. 23 illustrates one example of a usability simulation testing set-up.

Seven students, representing new users, were tested in a simulated environment (FIG. 23) to determine average time of assembly and number of errors during assembly. Ventilator sounds were played to simulate a patient's environment. Students were necessary for testing the new device to assess errors because people familiar with the old design have an inherent bias towards the old device. Students participated in six trials each and were given no information about device assembly. The OC was placed into the trach dummy and the other pieces placed beside the dummy. To limit learning bias, three students started with the prototype, and four started with the current device. The final five trials were randomly selected but so that each student assembled each device 3 times. The students were timed and the number of errors made throughout the assembly process were recorded. Before each trial, students played a computer game to simulate a working environment as usually nurses are not tending to a patient before an emergency. Each trial began at the sound of a ventilator alarm to simulate an emergency situation. Timing ended once the students placed their hands down on the table. The students were videotaped to identify common errors after testing. Student time and error was analyzed with a two-tailed paired t-test. A two-tailed independent t-test was done to compare students who began with the prototype to those that began with the current device. The means and standard deviations were calculated.

Success criteria for untrained usability was assembly time for the prototype being less than or equal to the current design and same or fewer number of assembly errors for threaded and BNC connections compared to the current design. There was no significant difference in assembly time for both the threaded and BNC connection compared to the clips and friction fit, respectively, as well as no significant difference in errors for the threaded connection compared to the clips, and fewer errors for the BNC connection compared to the friction fit. Overall, there were fewer assembly errors for our prototype compared to the current device.

Figure 24:
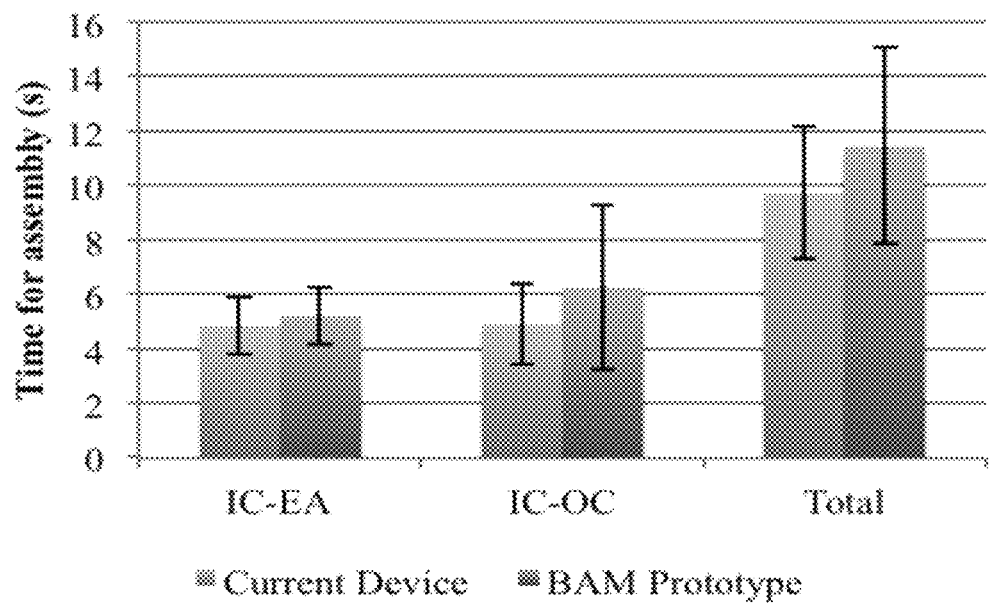
FIG. 24 is a graph showing assembly time testing for the IC-EA connection (prior art device), IC-OC connection (prototype device described herein), and total device across three attempts with the current device and prototype (n=6). Standard deviation bars are included.

The Grubbs' test for outliers (Gcrit=1.938) was conducted for the maximum and minimum values of the BAM prototype IC-OC assembly times. Two samples were discarded which resulted in a normal distribution. The two samples discarded were the maximum values for trial 1 (G=2.413) and trial 2 (G=2.014). No statistical difference was found between the assembly times with the current device and the BAM prototype for the IC-EA connection (p=0.365) and the IC-OC connection (p=0.846) as shown in FIG. 24.

There was no significant difference for the assembly time between the first and third attempts for the IC-EA connection ($p_{current}$=0.996, $p_{prototype}$=0.944) or the IC-OC connection ($p_{current}$=0.996, $p_{prototype}$=0.661). There was a decreasing trend in the required time for assembly of the IC-EA assembly, which may indicate that with training this assembly may be even more time efficient.

Figure 25:
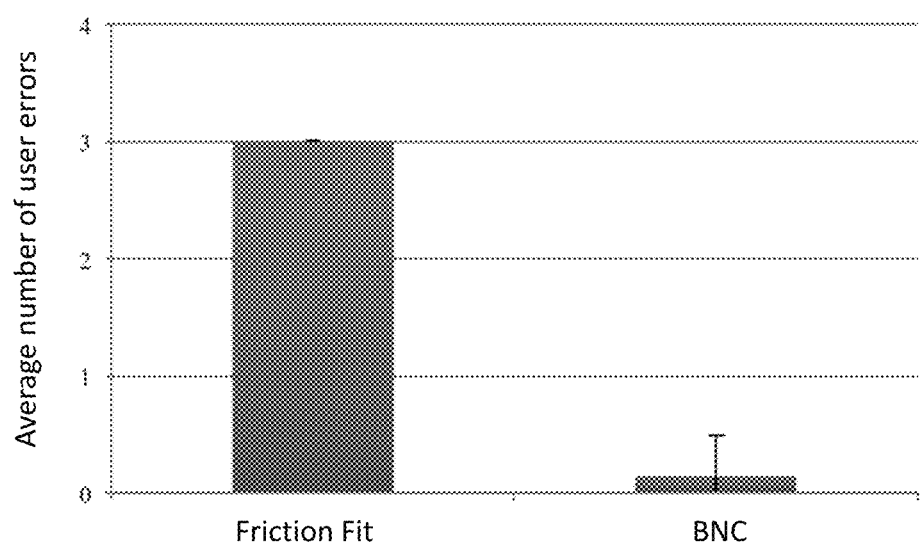
FIG. 25 is a graph comparing the average number of assembly errors between prior art devices ("friction fit") and the next-gen tracheal devices described herein (n=6).
Figure 26:
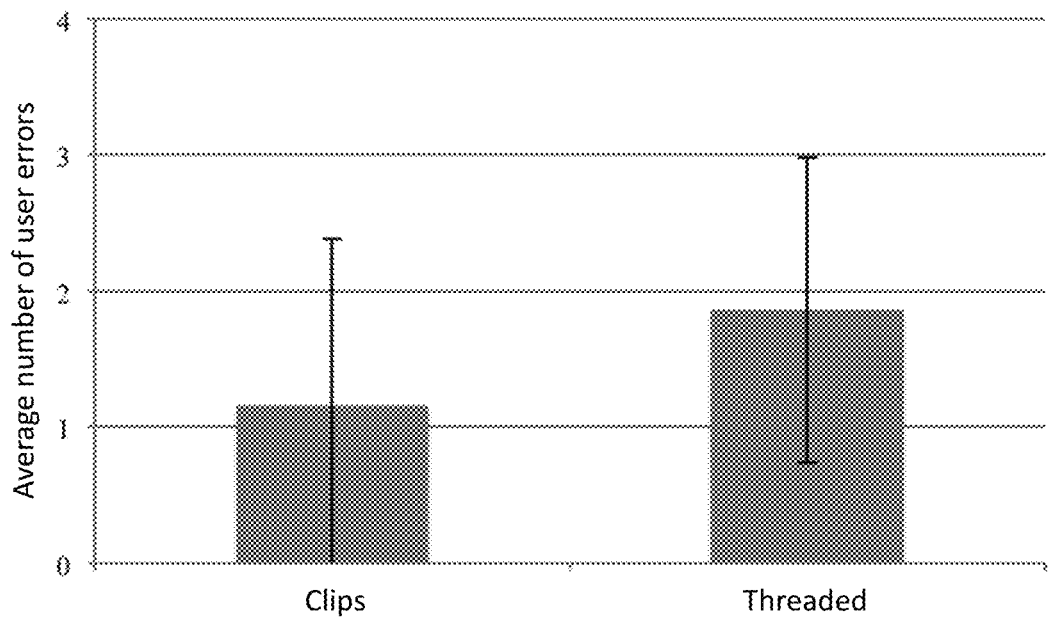
FIG. 26 is a graph comparing the average number of total assembly errors between prior art devices ("clips") and the threaded devices (prototype) as described herein.

The average number of total assembly errors per user for the IC-EA is shown in FIG. 25 and the IC-OC is shown in FIG. 26. Participants that made assembly errors made the same error across all attempts. All users made the mistake of not twisting the current IC-EA friction fit connection on all attempts (100%, 3 errors, S.D.=0). The average number of errors for the prototype was less than a third of the number of errors for the current device.

Only one user made a mistake using the prototyped IC-EA connection, by not fully twisting the connection. While the reason for this error could have been improper labeling, this error was only made once. There was no significant difference in number of assembly errors with the IC-OC between designs (p=0.782). For the current device, all of the IC-OC connection errors were that the clips were not properly secured until the EA was pressed on to the trach tube. For the BAM prototype, 92.3% of the IC-OC connection errors were lack of threading the cannula screw to the outer cannula. This could be due to unclear notification of complete threading.

Qualitative feedback was received on the current device and our prototype. From this, 67% of participants indicated that they preferred our prototype to the current. These results indicate that the majority of inexperienced users felt comfortable with assembling the BNC IC-EA connection over the friction fit; however it was suggested that labeling outside of the swivel with the twisting motion would be helpful. Most of the negative feedback was associated with the threaded IC-OC connection, where users found it unclear that the IC was meant to twist onto the OC for securement.

Usability: Trained Users

The purpose of this test was to determine the time required to disassemble then reassemble the prototype. The process was designed to mimic changing an IC, which is performed daily by care providers. The patient is disconnected from the ventilator for the entire process, so the exchange needs to be efficient because these patients have reduced lung capacity.

Six care providers, representing trained users, were tested to measure time of disassembly and assembly for the prototype. The layout of the test was similar to FIG. 23, except no sound was used. Care providers disassembled the device by removing the EA and IC from the trach dummy, then replaced the EA and IC to simulate changing the IC in a real patient. Three trials were performed by each subject.

Success was determined by the mean time for each subject being less than one minute. Mean and standard deviation of each subject was calculated as well as mean and standard deviation across all trials.

Figure 27:
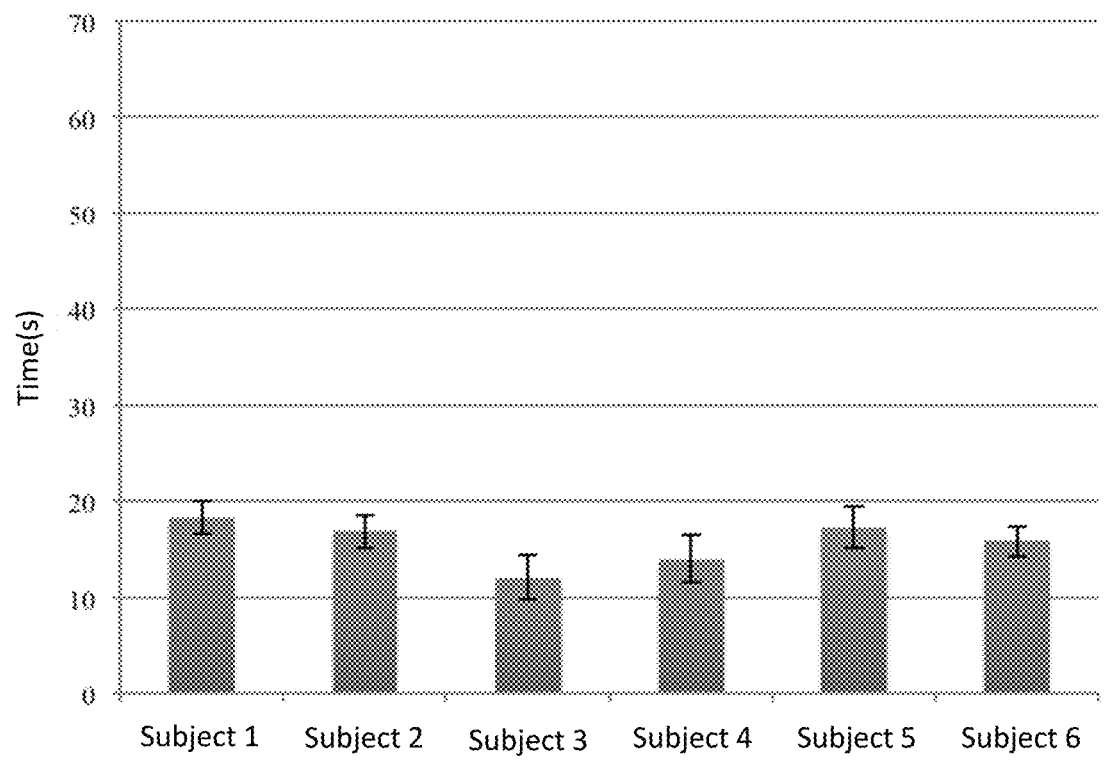
FIG. 27 is a graph illustrating average time for disassembly and assembly of the devices as described herein for each of the six sample subjects using the prototype apparatuses described herein.

For testing the time of assembly, six trained users (care providers) disassembled the device and reassembled the device to mimic changing the IC. FIG. 27 shows the results of the three trials from each subject. Each user was well under the 1 minute threshold. The average time across all trials was 15.75±2.76 s. The data shows that the device can be changed within 1 minute, meaning that the device is safe for patient use because oxygen levels would not get low enough to cause damage.

Pressure Valve Sensitivity

The purpose of this test was to determine if the pressure valve is sensitive enough to release air at high pressures but still prevent air release at safe air pressures. A specification for our prototype is tolerance of airflow in the range of 0-50 cm $H_2O$ but reject airflow at pressures of 65 cm $H_2O$ or greater. If pressure gets too high, lung and tissue damage can occur.

The prototype was connected to a mechanical ventilator, and the pressure settings on the ventilator were stepped from 30-70 cm $H_2O$ in increments of 5 cm $H_2O$. The prototype was tested at each pressure for five cycles. A piece of tissue paper was placed approximately 5 mm above the pressure valve, and it was noted when the piece of tissue paper moved upwards in response to airflow through the pressure valve.

In order for our pressure valve to be determined successful, zero activations must occur at pressures less than or equal to 50 cm $H_2O$, and a statistically significant larger amount of paper movements will need to be observed for pressure values greater than or equal to 65 cm $H_2O$ compared to 50 cm $H_2O$. The comparison was a two-tailed independent t-test.

Durability

The purpose of this test is to determine if the prototype and pressure valve are able to repeatedly and consistently function properly. Specification for our prototype include the prototype being able to last for 7-14 days and the pressure valve being able to maintain proper function for 7-14 days. These times are how long the current EA lasts before it is replaced.

The prototype was connected to the current ventilator and ventilator circuit and subjected to 100 ventilation cycles (approximately 5 minutes) at a normal air pressure of 60 cm $H_2O$. A normal cycle lasts about 3 s. Any cracks or failures were noted during this procedure. To test for pressure valve durability, the prototype was subjected to 50 cycles of low pressure ventilation (60 cm $H_2O$) followed by 50 cycles of high pressure ventilation (90 cm $H_2O$) to activate the valve. Tissue paper movement above the valve will once again note successful activation. Following this, another set of 50 cycles of low pressure and 50 cycles of high pressure were performed. The success criteria for valve durability was an active valve both the first and second set of 50 high-pressure ventilator cycles and a non-active valve for all low pressure cycles.

As mentioned above, PVC may be used in the final fabrication instead of VeroWhitePlus. PVC may be the final material choice as it is an FDA approved material for tracheostomy tubes. Injection molding may be used to increase manufacturing resolution, reduce costs, and begin mass production, instead of (or in addition to) 3D printing.

Figure 28:
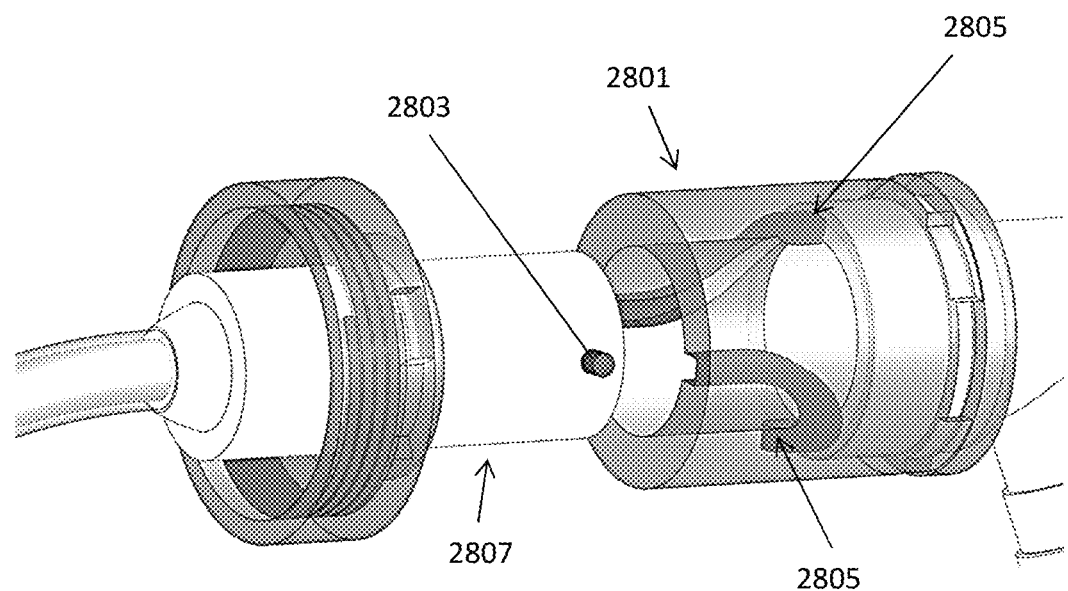
FIG. 28 illustrates one example of a next-gen trach tracheal device as described herein.

The apparatus may also include one or more labels, including labeling of the swivels to show which way pieces should turn. In usability tests, subjects had trouble twisting the threads and some with getting the pins lined up with the channels for the BNC connection. Labeling the outside of each swivel to show which way the swivels twist would make it easier to understand what needs to be done and indicate to users that twisting should occur. Additionally, to address the channel and pin alignment issue, the swivel head may be translucent so users can see the pins going into the channels and rotating properly into the groove and allow care providers to detect secretions in the ventilator circuit. The pins and channels may be colored, as seen in FIG. 28, to improve usability.

For example, in some variations, the inner and/or outer cannula may be transparent or translucent, and a portion (e.g., the pin) may be colored a first color (e.g., red, blue, yellow etc.). The BNC connector 2801 may also be generally translucent or transparent, and all or a portion (e.g., the end, locking, region) may be colored a different color (e.g., blue, red, yellow) from the pin or other portion of the outer cannula, so that the user can visually see, by the color change, that the pin is fully engaged by the BNC connector. In one example the inner cannula or counter cannula 2807 include a pin 2803 that is colored red and the BNC connector 2801 is translucent, but includes a region at the end of the BNC channel 2805 that is colored a different color from the pin, such as blue or yellow. When the pin 2803 is engaged in the locking position of the BNC 2805, the user will see a color indicator, as the pin will appear to change from red to purple (if the end or locking region of the BNC is blue) or orange (if the end or locking region is orange). Thus, in general, the apparatus may be configured so that engaging the BNC provides a visual indicator that the two are correctly engaged together.

In any of the variations described herein, the BNC connector and the threaded connector between the inner and outer cannula may be configured to be tightened by rotation in opposite directions or in the same direction. For example, the BNC connector may be configured to be secured by rotating clockwise (right) relative to the pin, while the threaded connector between the inner cannula and outer cannula may be configured so that this clockwise rotation tightens the connection between the inner and outer cannulas. Alternatively in some variations the threaded connection may be tightened by rotating the BNC connector in an opposite direction relative to the threaded connector (e.g., clockwise to tighten the BNC and counterclockwise to tighten the threaded connector).

During usability testing, care providers mentioned that being able to use an Ambu bag is important for changing cannulas. It uses a friction fit to connect to the IC. To address this problem, the BNC pins could be moved to allow for attachment around the BNC fit, or an adaptor could be included. The adaptor may have a friction fit on one end that attaches to the Ambu bag and the other end would have BNC channels to attach to the pins.

In order to design a more effective pressure valve, the friction between the seal and casing may be accounted for and optimized during engineering analysis of the pressure valve. The surface area of the seal may be increased in order to increase the force applied to the seal by airflow. This may help to overcome friction between the valve casing and seal. Additionally, a range of pressure release valves may be available to match the high pressure limit for individual patients. The current prototype was designed for our client's needs only.

Figure 29:
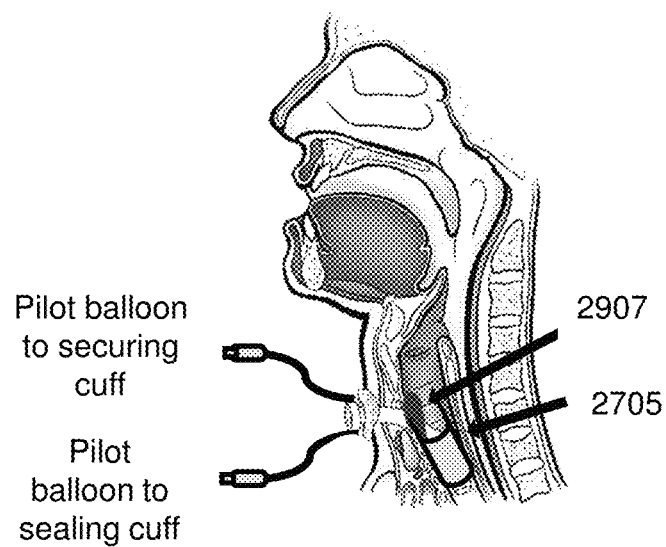
FIG. 29 illustrates one example of a double-cuff layout for a device configured as a tracheostomy tube.

Any of the apparatuses described herein may include one or more securing cuffs (e.g., balloon cuffs) on the outer and/or inner cannula. The use of one or more cuffs may prevent or reduce undesirable movement of the tracheal tube with respect to the user's body. For example, in FIG. 29, an embodiment including multiple securing cuffs is shown. In this exemplary securement design, a double cuff includes a first cuff ("sealing cuff") 2905 positioned midway along the outer cannula for securing the outer cannula within the trachea and second slightly proximal second cuff 2907 ("securing cuff") that is configured to be positioned within the trachea near or against the stoma. The second cuff may be configured to seal the stoma and support the ventilator circuit. The second cuff may be located in the trachea just behind the stoma and provide an opposing force to the weight of the ventilator circuit. These cuffs are configured in this example as balloons and may include inflation lines to separately or jointly inflate them.

Any of the apparatuses described herein may also include a harness comprising a neck strap adapted to hold the outer cannula of the tracheal tube securely within the patient's trachea. In general, this harness may be configured to be adjustably secured over the patient's torso, and may include one or more straps that fit over the subject's shoulders and under their arms to secure the tracheal tube within the patient's trachea. In some variations the harness includes adjustable straps having clips, belts, etc. for adjusting the fit to the patient. Alternatively or additionally the apparatus may include a garment, such as a shirt, including a neck strap or mount to which the rest of the tracheal tube may be coupled. The harness may include a garment (e.g., fabric covering the torso region), and/or may include one or more straps that may secure to the subject's torso. An example of a harness is shown in FIGS. 30A (front) and 30B (back). This variation of a securement design includes a shoulder harness 3005 (see, e.g., FIGS. 30A and 30B) having adjustable straps and one or more buckles/clips. Shoulder harness may also include one or more straps forming or connected to the neck strap. The neck strap region (or a neck region of the harness/garment) may include an interface (e.g., a faceplate) for securing to the tracheal tube, such as the region of a tracheal tube that is distal to the elbow joint, near the connection between the inner and outer cannulas. This design may reduce pressure on the neck and distribute the weight of the ventilator circuit over a larger area of the body, and may include a reusable harness with a back strap across the upper shoulders and two shoulder straps circle around each shoulder. The shoulder straps may be adjusted with buckles. Two disposable securement straps may attach the faceplate of the tracheostomy tube to the shoulder harness.

In addition, securement concepts that do not touch the patient's back or shoulders may be used, e.g., securement mechanisms around the ears or around the head of the patient.

To assess comfort, the force of assembly of the prototype may be lower than that required by the current system. The devices described herein may fully sterilizable via ethylene oxide or another chosen sterilization method.

The tracheostomy tube (IC and OC) and an EA described herein may replace the current standard device for ventilator dependent patients. The current clip connection between the IC and OC have been replaced with a threaded connection, and the current friction fit between the IC and EA with a BNC connection. These modifications were made to reduce unintended disconnections by improving usability, security, and comfort of the current connections.

A BNC to friction fit adaptor may be made to enhance compatibility with other prior art devices. Injection molding with PVC may be used to fabricate the design; the prototype may be manufactured using injection molding with PVC. In addition, alternative securement methods may be used. In addition, modifications of prototype measurements may be made to account for injection molding, labels and coloring for increased usability, a friction fit adaptor for the BNC connector, and modifications of the pressure valve design.

FIGS. 31-33B illustrate one variation of an apparatus, including exemplary dimensions (any of which may be adjusted to be +/−20%, +/−15%, +/−10%, +/−5%, +/−2%, etc.). For example, in FIG. 31, the exploded view shows the relationship between the outer cannula 3101, which may be attached to the subject through a faceplate 3103. In FIG. 31, the faceplate locks around the outer cannula portion, and the outer cannula portion may be coupled to a neck strap (and/or harness, as discussed and illustrated above). In FIG. 31 the faceplate assembles over the outer cannula by attaching two separate parts. The inner cannula 3105 is coupled to an inner cannula coupler 3107 that includes a ridge on the inner cannula distal end and is mounted to the inner cannula through a swivel piece that is configured to rotate around the at least one ridge. The swivel piece 3108 is external to the inner cannula and is configured to rotate relative to the inner cannula. The inner cannula coupler includes an inner threaded region that mates with a threaded region on lip of the outer cannula so that the two may connect and lock together by rotating the inner cannula coupler (e.g., clockwise), without rotating the inner cannula within the outer cannula. The very distal end of the inner connector is coupled to an extender 3109 that includes one or more, e.g., two, pins 3110 (or may include another member) for engaging the BNC connector 3113. In FIG. 31, the BNC connector is shown in two parts that can be formed over the elbow joint 3115 portion. The BNC connector includes tracks or channels for the pin(s) 3110 on the inner cannula. A connector 3111 for the respiratory device (e.g., respirator) is attached (or may be integral with) a bottom portion of the elbow joint, as shown. In this example, a pressure release valve is attached to the distal end of the apparatus and includes a pressure release casing 3123 with an aperture, a spring 3121, and a pressure release valve spring disc 3119, and is connected by a threading (including a washer 3117 or other sealing member) to the elbow joint.

Figure 32A:
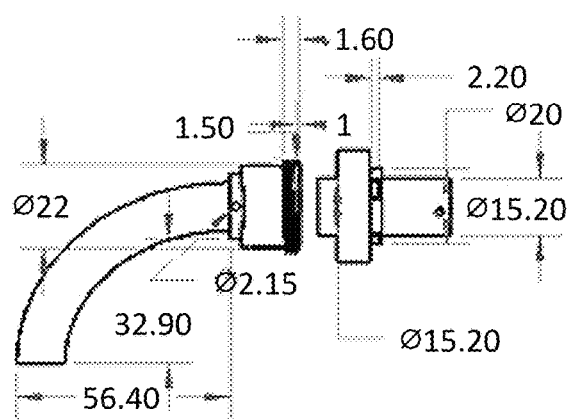
FIGS. 32A and 32B show side and top partially exploded views, respectively, of an outer cannula of a tracheal tube (e.g., tracheostomy and/or endotracheal tube) assembly and a portion of an inner cannula that mates with the outer cannula through a threaded connection. The dimensions shown on these components are exemplary only, and are provided in mm, or (as apparent from the context) degrees.
Figure 32B:
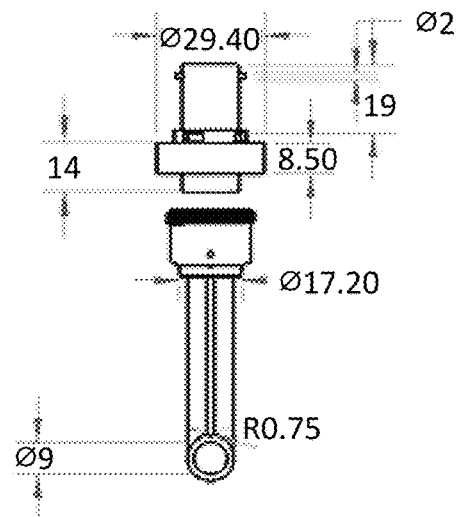
Figure 33A:
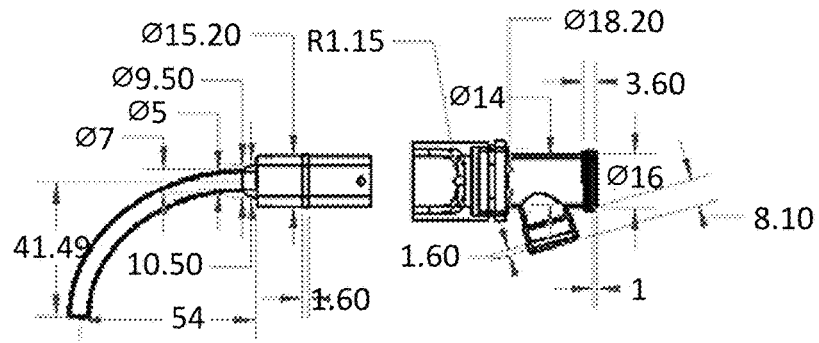
FIGS. 33A and 33B show side and top partially exploded views, respectively, of an inner cannula and an elbow joint and a BNC connector connecting between the two. The dimensions shown on these components are exemplary only, and are provided in mm, or (as apparent from the context) degrees.
Figure 33B:
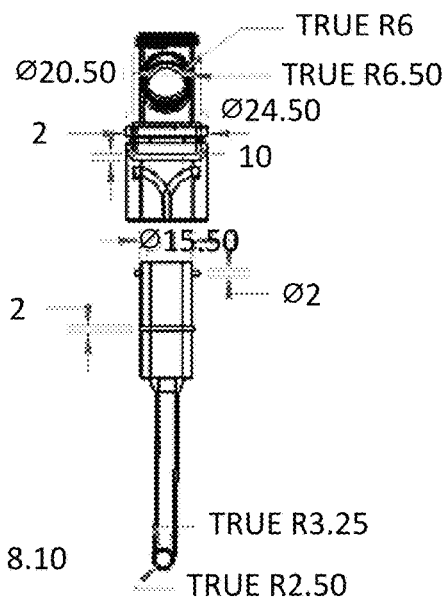

FIGS. 32A and 32B illustrate partially exploded schematics showing exemplary dimensions for the inner cannula and a portion of the outer cannula in mm. FIG. 32A shows a side view and FIG. 32B shows a top view. Similarly, FIGS. 33A and 33B show side and top partially exploded schematic views of an inner cannula, BNC connector and elbow joint with exemplary dimensions.

Figure 34A:
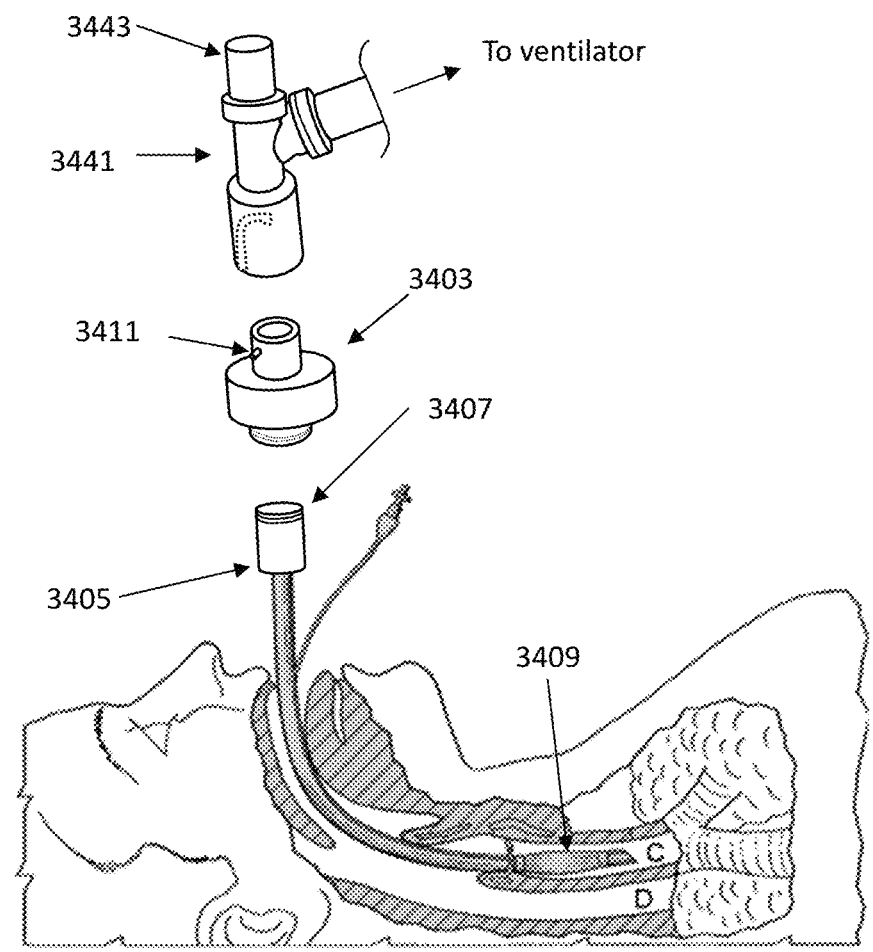
FIG. 34A shows an example of a tracheal tube system configured for use as an endotracheal tube system for insertion into the mouth (showing insertion into the patient's mouth) including an adapter and the elbow joint described herein.
Figure 34B:
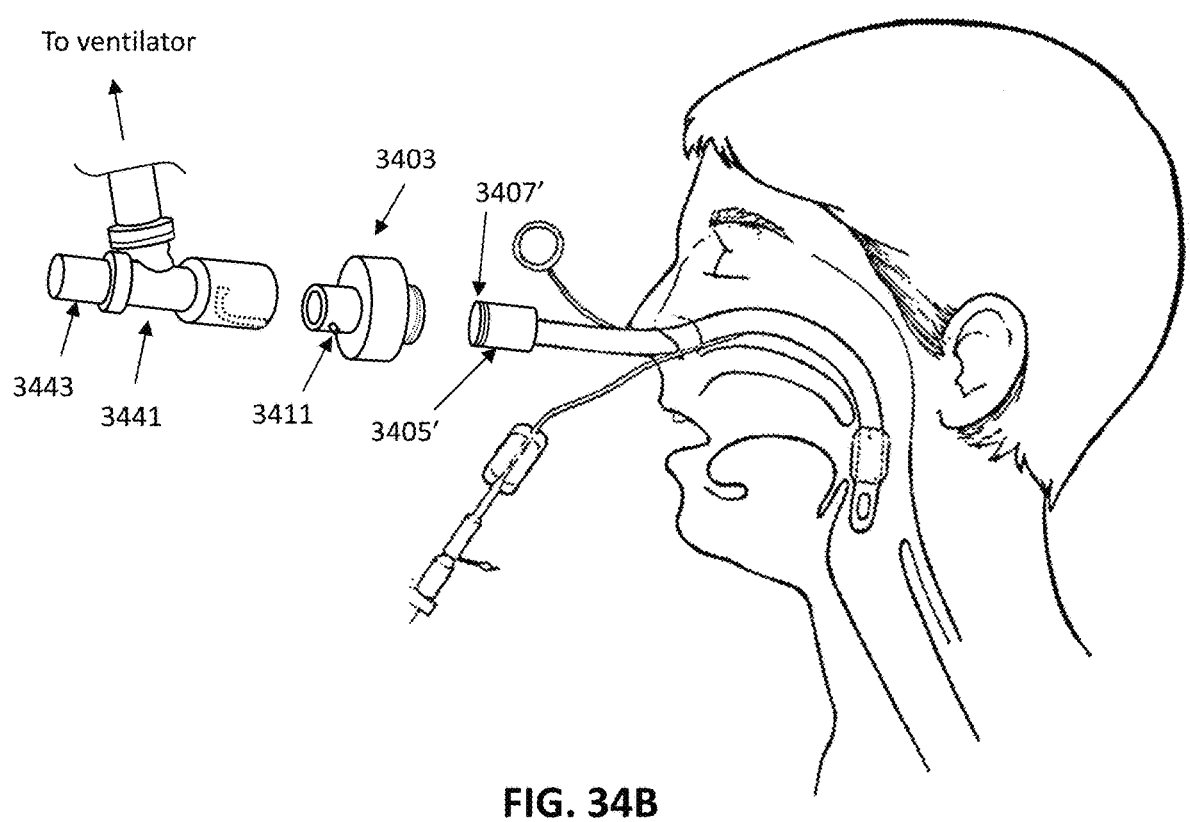
FIG. 34B shows an example of a tracheal tube system including an adapter configured for use as an endotracheal tube for insertion into the nose (showing insertion into the patient's nose).

Any of the tracheal tubes described herein may be configured as endotracheal tubes. For example, FIGS. 34A and 34B show examples of a tracheal tube apparatus (e.g., system) as described herein being inserted through a patient's mouth (FIG. 34A) and/or nose (FIG. 34B). In this example, the tracheal tube includes an inserting cannula 3405 having a proximal end and a distal end, the inserting cannula distal end having threads 3407. The threads may be at the very distal end (including the distal lip or separated from the distal lip by between 2-50 mm, e.g., between 5-10 mm, 5-20 mm, 5-25 mm, 5-30 mm, etc.). The inserting cannula may include an anchor (e.g., an inflatable region 3409) that helps secure the inserting cannula within the airway, which may be controllably inflated, self-expanding, etc.). The tracheal tube system shown may also include an adapter 3403 (BNC to threaded adapter) configured to attach onto the outer cannula and having a threaded region that mates with threads 3407 on the inserted cannula 3405. In some variations the threads are locking; thus the adapter is configured to be attached to the inserting cannula in a permanent or semi-permanent manner. The threads may lock and seal the adapter to the inserting cannula. In some variations the threads include an adhesive, alternatively or additionally, in some variations the threads include a locking feature such as a deformable material (e.g., nylon, etc.) that is deformed when the threads are engaged. The lock may be on the adapter and/or on the inserting cannula. The threads on the inserted cannula 3405 may be on the outside (as shown in FIG. 34A) to mate with thread on the inside of the adapter 3403, or the threads on the inserted cannula 3405 may be on the inside of the cannula and made with threads on an outside of the adapter 3403. The adapter includes an inner lumen that is continuous with and sealed to the inner lumen of the inserted cannula 3405. The adapter also includes a Bayonet Neill-Concelman (BNC) connector (a pair of pin portions 3411, only one is visible) on a distal end of the adapter 3403) that is configured to secure the adapter to the elbow adapter.

In FIG. 34A, the apparatus also includes an elbow adapter 3441 with a pressure release valve 3443 as described above, e.g., on the elbow adapter configured to mitigate high airway pressures that may cause disconnections or lung damage. In any of these apparatuses, the pressure release valve may be set to a fixed trigger (e.g., release/opening) pressure or may be adjustable to a trigger pressure or range of trigger pressures. The elbow adapter portion of the system shown in FIG. 34A also includes a Bayonet Neill-Concelman (BNC) connector for mating with the pin portion 3411 of the adapter 3403 and may be configured to secure the elbow adapter 3441 to the inserted cannula 3405. In some variations, the locking region of the BNC is transparent or translucent and is configured to change color when the BNC is engaged with the inner cannula.

FIG. 34B shows a similar example of a tracheal tube system including an endotracheal tube inserted into the patient's nose. As described in FIG. 34A, the tracheal tube includes an inserting cannula 3405' having an inserting cannula proximal end and an inserting cannula distal end, the distal end having outer cannula threads 3407' (as mentioned above, in some variations the threads may be internal to the distal end of the inserting cannula). The inserting cannula threads may be at the very distal end (including the distal lip or separated from the distal lip by between 2-50 mm, e.g., between 5-10 mm, 5-20 mm, 5-25 mm, 5-30 mm, etc.). The tracheal tube apparatus shown therefore includes an adapter 3403 configured to adapt an elbow connector 3441 to the inserting cannula 3405', the inserting cannula distal end having a coupler (which may be threaded, as described above) for mating with a threaded region of the adapter 3403. The apparatus may also include an elbow adapter 3441 configured to couple the inserting cannula (via the adapter) with a mechanical ventilator for providing air to a patient (not shown). The elbow adapter (or in some variations the adapter 3403, 3403) may include a pressure release valve, as described above, e.g., configured to mitigate high airway pressures that may cause disconnections or lung damage. The apparatus shown in FIG. 34B also includes a Bayonet Neill-Concelman (BNC) connector (the pin portion 3411 is shown on the adapter 3403) configured to secure the elbow adapter 3441 to the inserting cannula. In some variations, the locking region of the BNC is transparent or translucent and is configured to change color when the BNC is engaged with the inner cannula. The endotracheal tubes described herein may include any of the features of the tracheal tubes described above (including features of the tracheostomy examples).

Figure 35A:
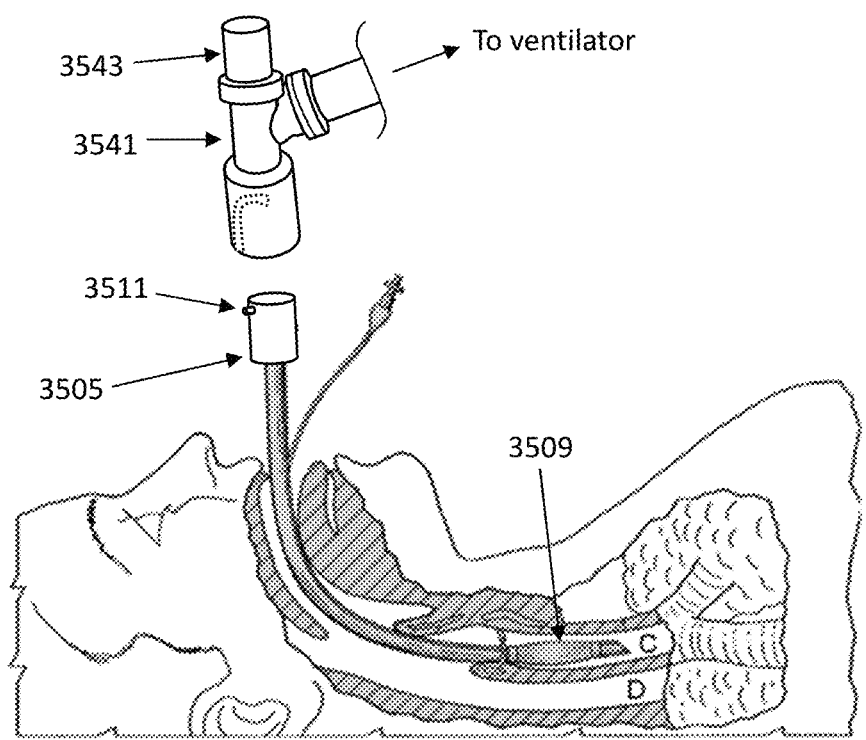
FIG. 35A shows an example of a tracheal tube system configured for use as an endotracheal tube system for insertion into the mouth (showing insertion into the patient's mouth) including an elbow joint described herein.
Figure 35B:
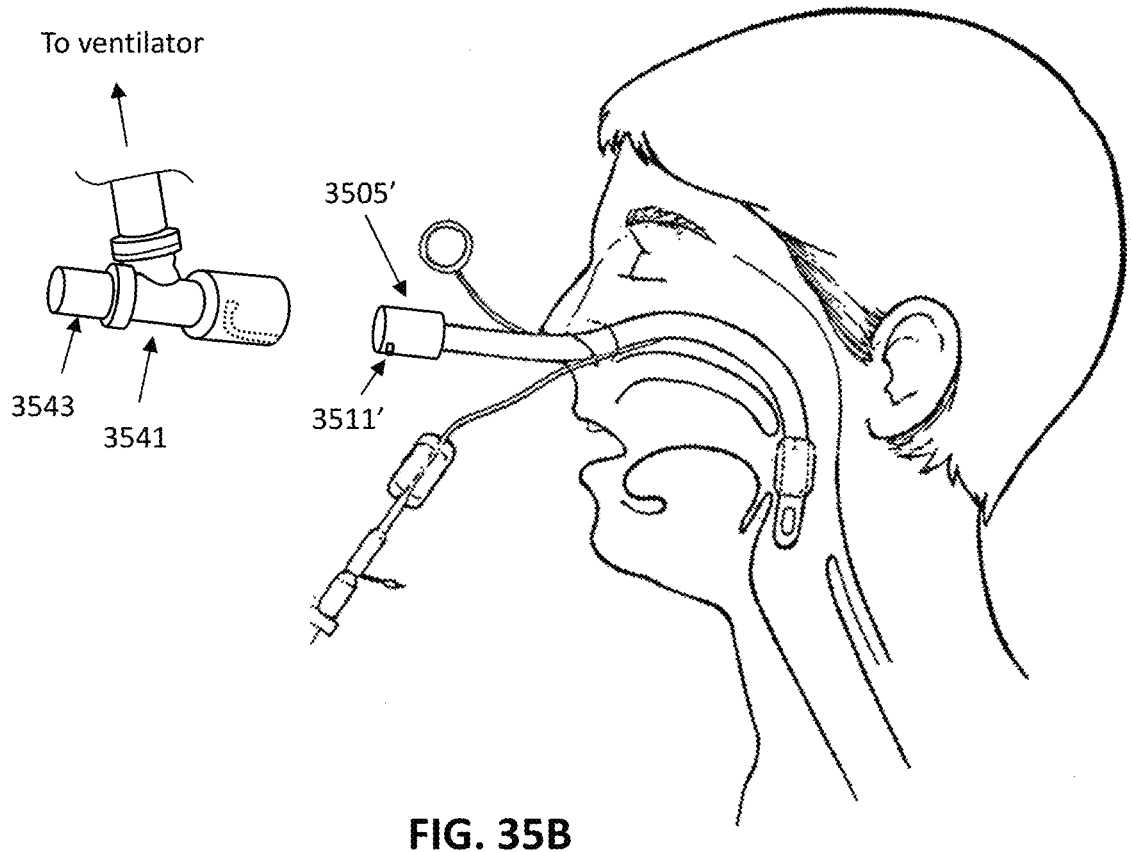
FIG. 35B shows an example of a tracheal tube system configured for use as an endotracheal tube for insertion into the nose (showing insertion into the patient's nose).

FIGS. 35A and 35B illustrate a variation in which the endotracheal tube itself includes the BNC connector the (pin portion 3511, 3511'), rather than include a separable adapter as shown in FIGS. 34A-34B. In FIGS. 35A and 35B the examples of a tracheal tube apparatus (e.g., system) are inserted through a patient's mouth (FIG. 35A) and/or nose (FIG. 35B). In this example, the tracheal tube includes an inserting cannula 3505, 3505' having a proximal end and a distal end, the inserting cannula distal end having a BNC connecting pin (or multiple pins) 3511, 3511'. The pin(s) may be at the very distal end (including the distal lip or separated from the distal lip by between 2-50 mm, e.g., between 5-10 mm, 5-20 mm, 5-25 mm, 5-30 mm, etc.). The inserting cannula may include an anchor (e.g., an inflatable region 3509) that helps secure the inserting cannula within the airway, which may be controllably inflated, self-expanding, etc.).

In FIG. 35A, the apparatus also includes an elbow adapter 3541 with a pressure release valve 3543 as described above, e.g., on the elbow adapter configured to mitigate high airway pressures that may cause disconnections or lung damage. In any of these apparatuses, the pressure release valve may be set to a fixed trigger (e.g., release/opening) pressure or may be adjustable to a trigger pressure or range of trigger pressures. The elbow adapter portion of the system shown in FIG. 35A also includes a Bayonet Neill-Concelman (BNC) connector for mating with the pin portion(s) 3511 of the inserting cannula 3505 and may be configured to secure the elbow adapter 3541 to the inserted cannula 3505. In some variations, the locking region of the BNC is transparent or translucent and is configured to change color when the BNC is engaged with the inner cannula.

FIG. 35B shows a similar example of a tracheal tube system including an endotracheal tube inserted into the patient's nose. As described in FIG. 35A, the tracheal tube in FIG. 35B includes an inserting cannula 3505' having a proximal end and a distal end, the distal end having one or more pins 3511'. The inserting cannula pins may be at the very distal end (including the distal lip or separated from the distal lip by between 2-50 mm, e.g., between 5-10 mm, 5-20 mm, 5-25 mm, 5-30 mm, etc.). The tracheal tube apparatus shown is configured to connect to an elbow connector 3541. The apparatus may also include an elbow adapter 3541 configured to couple the inserting cannula with a mechanical ventilator for providing air to a patient (not shown). The elbow adapter may include a pressure release valve, as described above, e.g., configured to mitigate high airway pressures that may cause disconnections or lung damage. The apparatus shown in FIG. 35B also includes a Bayonet Neill-Concelman (BNC) connector (the pin portion 3411 is shown on the inserting cannula 3505') configured to secure the elbow adapter 3541 to the inserting cannula. In some variations, the locking region of the BNC is transparent or translucent and is configured to change color when the BNC is engaged with the inner cannula. The endotracheal tubes described herein may include any of the features of the tracheal tubes described above (including features of the tracheostomy examples).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A tracheal tube assembly comprising:
   an inserting cannula having a proximal end and a distal end, the distal end having two or more pins extending laterally from a sidewall of the distal end; and
   an elbow adapter configured to couple the inserting cannula with a mechanical ventilator for providing air to a patient;
   a pressure release valve on the elbow adapter configured to mitigate high airway pressures that may cause disconnections or lung damage; and
   a Bayonet Neill-Concelman (BNC) connector configured to secure the elbow adapter to the inserting cannula, wherein a locking region of the BNC connector is transparent or translucent and is configured to change color when the BNC connector is engaged with the inserting cannula, wherein the BNC connector comprises two or more channels on the elbow adapter configured to mate with the two or more pins on the inserting cannula, wherein the two or more channels are arcs that are curved 90 degrees or more and extend longitudinally.

2. The tracheal tube assembly of claim 1, wherein the pressure release valve comprising a casing with an aperture, a spring, and a pressure release valve spring disc.

3. The tracheal tube assembly of claim 2, further comprising a seal mated with the pressure release valve spring disc, wherein the seal is configured to push back at high air pressures, compress the spring, and allow air to escape through the aperture.

4. The tracheal tube assembly of claim 1, wherein the pressure release valve comprises a variety of selectable pressure release settings.

5. The tracheal tube assembly of claim 1, wherein the pressure release valve is coupled to the elbow adapter through a pressure release valve-elbow adapter threaded connection.

6. The tracheal tube assembly of claim 1, further comprising a ventilator-elbow adaptor connection that is adapted to swivel.

7. The tracheal tube assembly of claim 1, wherein the BNC connector of the elbow adapter is configured to connect to the inserting cannula with a connection strength of greater or equal to 45 N.

8. The tracheal tube assembly of claim 1, further comprising a pair of laterally offset cuffs on the inserting cannula configured to seal and secure the inserting cannula within the patient's trachea.

9. A tracheal tube assembly comprising:
   an inserting cannula having a proximal end and a distal end, the distal end having two or more pins extending laterally from a sidewall of the distal end;
   an elbow adapter configured to couple the inserting cannula with a mechanical ventilator for providing air to a patient;
   a Bayonet Neill-Concelman (BNC) connector on the elbow adapter configured to secure the elbow adapter to the inserting cannula wherein a locking region of the BNC connector is transparent or translucent and is configured to change color when the BNC connector is engaged with the inserting cannula, wherein the BNC connector comprises two or more channels on the elbow adapter configured to mate with the two or more pins on the inserting cannula, wherein the two or more channels are arcs that are curved 90 degrees or more and extend longitudinally; and
   a pressure release valve on the elbow adapter configured to release excess pressure to mitigate high airway pressures that may cause disconnections or lung damage, wherein the pressure release valve is configured to release pressure above 65 cm $H_2O$.

10. The tracheal tube assembly of claim 9, wherein connection between inserting cannula and the elbow adapter has a connection strength of greater or equal to 45 N.

11. A method of using a tracheal tube within a patient, the method comprising:
   inserting a cannula into a patient's mouth or nose, wherein the cannula has a proximal end and a distal end, the distal end having two or more pins extending laterally from a sidewall of the distal end;
   coupling an elbow adapter to the cannula through a Bayonet Neill-Concelman (BNC) connection, wherein the elbow adapter is coupled to a mechanical ventilator through an elbow adapter-ventilator connection, wherein the BNC connection comprises two or more channels on the elbow adapter configured to mate with the two or more pins on the inserting cannula, wherein the two or more channels are arcs that are curved 90 degrees or more and extend longitudinally; and
   operating the tracheal tube so that a force greater than or equal to 45 N must be applied to separate the cannula from the elbow adapter.

12. The method of claim 11, wherein inserting the cannula comprises inserting into the patient's mouth.

13. The method of claim 11, further comprising a pressure release valve comprises a casing with an aperture, a spring, and a pressure release valve spring disc.

14. The method of claim 13, wherein the pressure release valve comprising a seal mated with the pressure release valve spring disc, wherein the seal is configured to push back at high air pressures, compress the spring, and allow air to escape through the aperture.

15. The method of claim 11, wherein operating the tracheal tube comprises releasing pressure above 65 cm $H_2O$ from a pressure release valve.

* * * * *